US012611148B2

(12) United States Patent (10) Patent No.: US 12,611,148 B2

Harpaz et al. (45) Date of Patent: Apr. 28, 2026

(54) SYSTEMS AND METHODS FOR SPECT DETECTOR CALIBRATION

(71) Applicant: GE Precision Healthcare LLC, Wauwatosa, WI (US)

(72) Inventors: Roi Harpaz, Center District (IL); Leonid Tsukerman, Haifa District (IL); Yaron Hefetz, Herzeliya (IL)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 385 days.

(21) Appl. No.: 18/311,727

(22) Filed: May 3, 2023

(65) Prior Publication Data

US 2024/0369725 A1     Nov. 7, 2024

(51) Int. Cl.
   *A61B 6/03*        (2006.01)
   *G01T 1/29*        (2006.01)
   *G01T 7/00*        (2006.01)

(52) U.S. Cl.
   CPC ............ *A61B 6/037* (2013.01); *G01T 1/2985* (2013.01); *G01T 7/005* (2013.01)

(58) Field of Classification Search
   CPC ...................................................... A61B 6/037
   See application file for complete search history.

(56) References Cited

U.S. PATENT DOCUMENTS

| | | | |
|---|---|---|---|
| 6,201,247 B1 * | 3/2001 | Lutheran ............... | G01T 1/1648 |
| | | | 250/363.04 |
| 7,633,057 B2 | 12/2009 | Cooke et al. | |
| 10,478,133 B2 | 11/2019 | Levy et al. | |
| 2006/0284065 A1 * | 12/2006 | Kasper ................... | A61B 6/586 |
| | | | 250/252.1 |
| 2011/0147574 A1 | 6/2011 | Blevis et al. | |
| 2012/0002857 A1 * | 1/2012 | Song ...................... | A61B 6/032 |
| | | | 382/131 |
| 2015/0173696 A1 | 6/2015 | Zingerman | |
| 2019/0209108 A1 | 7/2019 | Grobshtein et al. | |
| 2021/0247530 A1 * | 8/2021 | Li .......................... | G01T 1/249 |

FOREIGN PATENT DOCUMENTS

CN            101046513 A     10/2007

* cited by examiner

*Primary Examiner* — Uzma Alam
*Assistant Examiner* — Shun Lee
(74) *Attorney, Agent, or Firm* — McCoy Russell LLP

(57)                    ABSTRACT

Methods and systems are provided for calibrating a single photon emission computed tomography (SPECT) imaging system. In one example, a collimated line source for calibrating a SPECT system comprises a radioactive material aligned along a central axis of the collimated line source and a plurality of collimator plates arranged perpendicularly around the central axis, the collimator plates including a material that substantially absorbs photons striking the collimator plates. The collimator plates may absorb photons emitted by the radioactive material in non-perpendicular directions, which are not used for calibrating the SPECT imaging system, thereby reducing an amount of radiation released in an environment of the SPECT imaging system during calibration. Due to the reduced amount of radiation to which people in the environment are exposed, short time increments between patient examinations may be advantageously used to collect calibration data, reducing an overall amount of time used for calibration.

18 Claims, 15 Drawing Sheets

SYSTEMS AND METHODS FOR SPECT DETECTOR CALIBRATION

TECHNICAL FIELD

Embodiments of the subject matter disclosed herein relate to nuclear medicine imaging systems, and more particularly, to calibration and quality control of single photon emission computed tomography (SPECT) imaging systems.

BACKGROUND

Nuclear medicine (NM) imaging systems such as single photon emission computed tomography (SPECT) imaging systems may be used to diagnose certain disorders of a heart, brain, or other system of a patient. A radioactive substance may be introduced into the patient, which may be absorbed in a target organ or area of a body of the patient. The radioactive substance emits photons, which are collimated and detected by a detector subsystem. Detectors of the subsystem may generate output electrical signals from which three-dimensional (3D) images can be created, where the 3D images show a distribution of the radioactive substance in and around the target organ or area. Examining the distribution may aid a caregiver in diagnosing or monitoring a disorder of the patient. For example, the images may be used to diagnose clogged arteries, bone healing, seizures, cancer progression, or other problems.

Because physical values of a SPECT system (e.g., gain, baseline, sensitivity of each pixel, etc.) may vary across pixels of the detectors, one or more calibration maps may be used to correct an image post reconstruction. The calibration maps are files of measured or calculated parameters used to correct for differences in the physical values of the SPECT system. Correcting the reconstructed image may increase the uniformity of the image and/or decrease an amount of noise artifacts in the image. For example, an accuracy of an energy of the SPECT system may be maintained by using an energy correction map that compensates for variations in performance of different pixels of one or more detector arrays of the SPECT system. A uniformity of a resulting image (e.g., ensuring that a uniform subject will be seen as a uniform image) may be achieved by a uniformity correction map.

A daily quality control (DQC) may be performed on the SPECT system to ensure that the system is functional. If the DQC does not meet a threshold performance, a calibration of the SPECT system may be performed to ensure accurate and uniform energy readings. Additionally, periodic calibrations may be performed on the SPECT system.

During calibration, the physical values of the system may be measured, and the values of the calibration maps may be updated. Changes and drift of the physical values may cause inaccuracy of the calibration maps, and thus may cause artifacts in images generated by the SPECT system, and/or non-uniform images, which may increase a difficulty of analyzing the images. If a change in a calibration map is detected that exceeds a threshold change, one or more detector modules may be replaced, which increases a cost and an amount of downtime of the SPECT system.

Calibration may rely on collecting a large amount of statistical data, which may take several hours, during which the SPECT system may not be useable on patients. Additionally, since radioactive emission is a stochastic process, a statistical noise may be associated in the measurements of system performance. This noise may be translated into noisy calibration maps, which results in inaccurate correction of the diagnostic data, which may poor image quality image.

The weaker the calibration source, the longer it takes to collect sufficient calibration statistics. Further, during calibration, a radioactive source is introduced into the SPECT system, which exposes a room of the SPECT system to radiation. Because of the radiation, operators, technicians, caregivers, and/or patients may not be able to access the room during the calibration. As a result, performing the calibrations reduces an efficiency of use of the SPECT system, and may cause scheduling delays.

SUMMARY

The current disclosure at least partially addresses one or more of the above identified issues by using a collimated line source of radiation for calibrating a single photon emission computed tomography (SPECT) imaging system, the collimated line source comprising a radioactive material aligned along a central axis of the collimated line source and a plurality of collimator plates arranged perpendicularly around the central axis, the collimator plates including a material with an atomic number and a density to substantially absorb photons striking the collimator plates. The collimator plates may absorb photons emitted by the radioactive material in non-perpendicular directions, which are not used for calibrating the SPECT system, thereby reducing an amount of radiation released in an environment of the SPECT system during calibration. Due to the reduced amount of radiation to which people in the environment are exposed, operators, technicians, caregivers, and/or subjects may be present in the environment of the SPECT system during the calibration of the SPECT system, increasing an efficiency of use of the SPECT system. As a result of an increased availability and more efficient use of SPECT-based resources, a throughput of the SPECT system (e.g., a number of patients examined during a period of time) may be increased, generating less delays and better patient experiences.

Additionally, short time increments between patient examinations may be advantageously used to collect calibration data, and reducing an overall amount of time used for calibration. In other words, rather than scheduling a dedicated amount of time for collecting calibration data and performing the calibration, the calibration data may be collected piecemeal over several sessions, each lasting a small amount of time when the SPECT system is not being used. When a sufficient amount of calibration data has been collected and aggregated, the calibration maps of the SPECT system may be updated using the aggregated calibration data. A typical amount of time used to collect enough statistics for energy and uniformity calibrations may be long (e.g., more than an hour). However, once the data has been collected, a processing time is typically short (e.g., one minute). Thus, as a result of the piecemeal collection of calibration data when the SPECT system is not being used, an availability of the SPECT system for patient examinations may be increased, while reducing the amount of radiation to which people near the SPECT system are exposed.

The above advantages and other advantages, and features of the present description will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

Various aspects of this disclosure may be better understood upon reading the following detailed description and upon reference to the drawings in which.

Figure 1A:
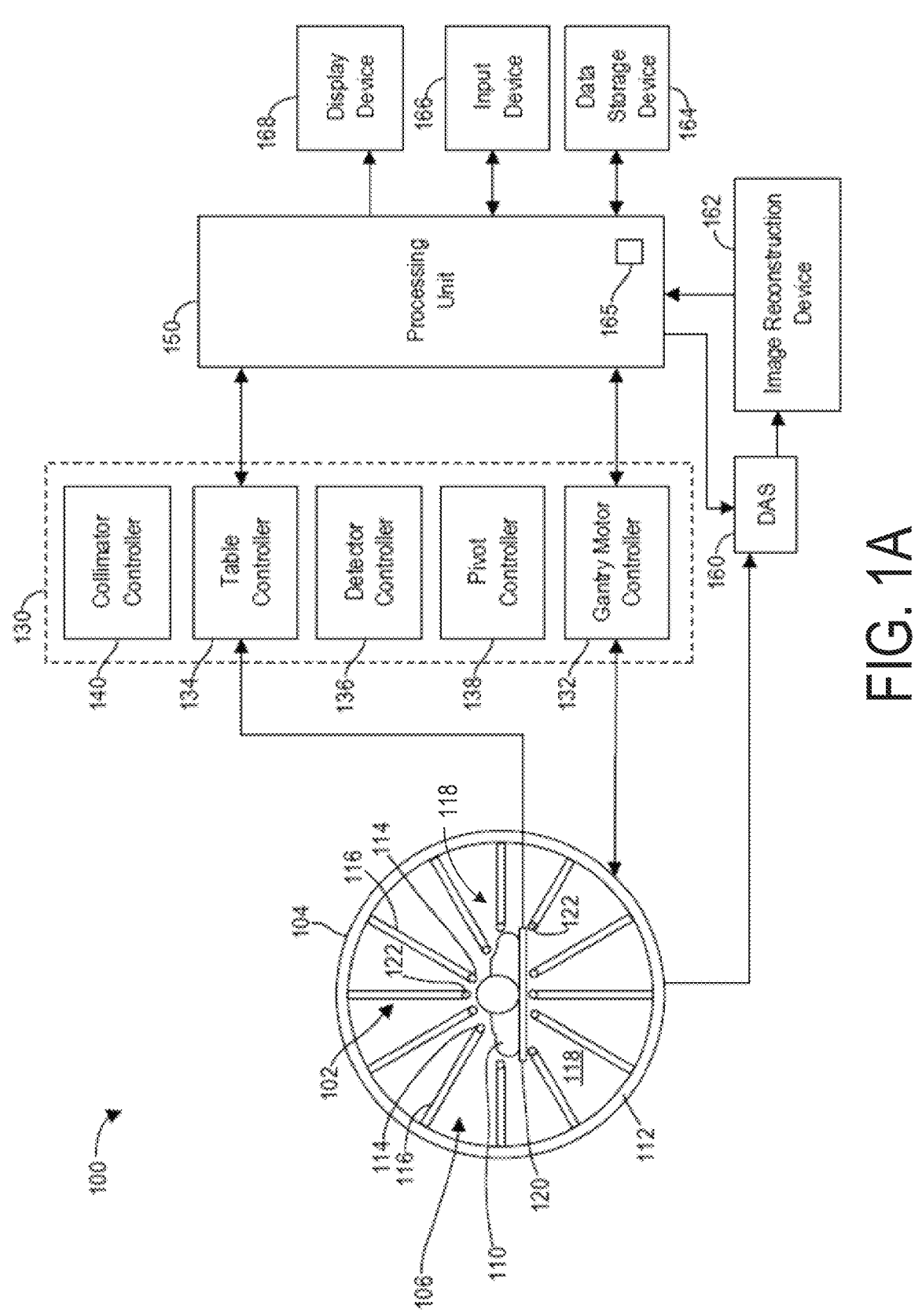
FIG. 1A is a schematic block diagram of a nuclear imaging (NM) imaging system, in accordance with an embodiment.

The drawings illustrate specific aspects of the described systems and methods. Together with the following description, the drawings demonstrate and explain the structures, methods, and principles described herein. In the drawings, the size of components may be exaggerated or otherwise modified for clarity. Well-known structures, materials, or operations are not shown or described in detail to avoid obscuring aspects of the described components, systems and methods.

DETAILED DESCRIPTION

This description and embodiments of the subject matter disclosed herein relate to methods and systems for a single photon emission computed tomography (SPECT) system. In particular, the methods and systems are proposed to increase an efficiency of use and an availability of the SPECT system, by reducing an amount of time spent periodically recalibrating the SPECT system.

A SPECT system shows a distribution of a radioactive substance inside a patient's body. A radioactive tracer (e.g., a source of penetrating radiation) is administered to the patient, which typically includes a pharmaceutical tagged with a radionuclide which emits radiation photons (radiopharmaceutical). The radiopharmaceutical is designed to be absorbed in a target organ, such as the heart muscle, or other organs or body part of interest. One or more detector arrays may be rotated about a gantry within an imaging plane and around the patient, and images are generated from the radiation photons at a plurality of views at different view angles. Additionally, some SPECT systems may include detector arrays with multiple detector heads, where each detector head may rotate or pivot, in addition to the gantry rotation. The emitted radiation photons are collimated with a collimator subsystem and detected by a detector subsystem which generates output electrical signals. The electrical signals are digitized and processed by a computer system to generate images of a regional distribution of the radioactive sources in and around the target organ.

The SPECT system may be periodically calibrated, to ensure that an amount of radiation recorded by detectors of the SPECT system is the same as an actual amount of radiation generated by radioactive tracer introduced into patients. During calibration, one or more calibration maps of the SPECT system may be updated. The calibration maps include correction values to be applied to detector outputs to correct for variance in pixel-level output.

The SPECT system may be calibrated using a standard source of radiation, such as Co-57, that emits photons at a known rate. The source of radiation may be a point source, where the radiation is emitted spherically outward from radioactive material at a single location, or the source of radiation may be a line source, where the radiation is emitted outward in all directions from radioactive material extending along a line of a given length. The length may be as long as or slightly longer than a length of a detector in a same dimension, such that the calibration process may be performed without having to move the line source along the length of the detector. In one example, the length of the line source is 28 cm, corresponding to 7 CZT detector modules with lengths of 4 cm each. An advantage of the line source over the point source with respect to calibrating the SPECT system is that radiation may be detected more evenly along length of the one or more detector arrays between collimators of the detector arrays. In some dual-head SPECT systems, the point source may be used when collimators are removed from the detectors. In multi-head SPECT systems, the point source may be used for a different mechanical calibration process.

Prior to calibration, the line source may be stored in a shielded container, to prevent an environment (e.g., a room including the SPECT system) of the line source from being exposed to radiation emitted by the line source. During calibration, the line source may be manually removed from the shielded container, and placed within the gantry. The gantry may be rotated and the detector arrays of the SPECT system may detect radiation photons emitted by the line source as the detector arrays move around the line source. The line source emits radiation at a consistent energy peak or small number of peaks, such that the detector arrays of the SPECT system may be calibrated with reference to the consistent energy peak. For example, Co-57 peaks at 122 KeV. When the calibration is performed, technicians and/or other humans in the room may leave the room to avoid radiation exposure, or a shield may be placed between the SPECT system and the technicians to protect the technicians from being exposed to the radiation.

Calibrating the detector arrays of the SPECT system may be time-consuming, given that a precision of the calibration may depend on a sufficient number of radiation photons being detected by a large number of individual detector elements distributed across the detector arrays. During the calibration, the room may not be used, due to a risk of radiation exposure. After the calibration has ended, the line source may be manually removed from the gantry of the SPECT system and placed back in the shielded container for storage. After the line source is placed within the shielded container, the technicians and/or other humans may reenter the room and the SPECT system may be used for patient examinations.

During calibrations, statistical (e.g., photon) data may be collected over a period of time, and calibration maps of the SPECT system may be updated based on collected statistical data. During the DQCs, a relatively small amount of statistical data may be collected, whereby the DQCs may have a short duration. For example, photon counts may not be collected at every detector element of the detector arrays during the DQCs, and/or a number of photon counts collected at the detector elements may be small in comparison to a calibration. In one example, a duration of a DQC may be 15-30 min, depending on source activity. As a result, the DQCs may not affect an availability of SPECT system for patient examinations to a large degree.

During the calibrations, a larger amount of statistical data may be collected, whereby the calibrations may have a longer duration. For example, a greater number of photon counts may be collected at every detector element of the detector arrays during the periodic calibrations, as compared to the DQCs. For example, 10 times more data may be collected during a periodic calibration than during a DQCs. In one example, a duration of a calibration may be one or more hours. As a result, calibrating the SPECT system may generate significant amounts of time during which the SPECT system may not be used for patient examinations or other purposes.

Because the detectors of the SPECT system are collimated, each pixel of each detector measures photons entering at a narrow perpendicular angle to a surface of the detector. However, photons generated by the line source may be directed in a plurality of directions away from the line source. Therefore, during calibration, a very small proportion (e.g., 0.0002) of the photons emitted by the source will reach a radiation-sensitive portion of a detector. A small fraction of photons will be emitted at the narrow perpendicular angle to the detector, and will be used to calibrate the SPECT system. The rest of the photons will generate radiation in the room, but will not be used for calibration.

Because photons emitted by the line source in non-perpendicular directions are not recorded during calibration, the inventors herein propose a novel configuration of the line source including collimators. The proposed collimated line source may emit radiation photons in a perpendicular direction, and may not emit radiation photons in non-perpendicular directions. As a result, the amount of radiation generated in areas of the room of the SPECT system during calibration may be reduced. Due to the reduced amount of radiation to the room areas, people may enter and use the room areas, increasing an efficiency of use of the SPECT system.

Additionally, the collimated line source may be used to collect calibration data at any time a patient is not being scanned by the SPECT system. Short amounts of time between patient scans may be advantageously used for collecting the calibration data in a piecemeal fashion. In other words, the acquisition of calibration data may not be performed during a single, longer duration where the SPECT system is unavailable for examinations. Rather, a plurality of calibration acquisition sessions may be performed during one or more days, taking advantage of short periods of waiting time (e.g., 5-10 minutes) between patient scans. The calibration data may be aggregated and used to update the calibration maps of the SPECT system at a later time, reducing an overall amount of time used for performing the calibration. Additionally, the collected calibration data can also be used retroactively to correct images, prior to performing the calibration.

Figure 1B:
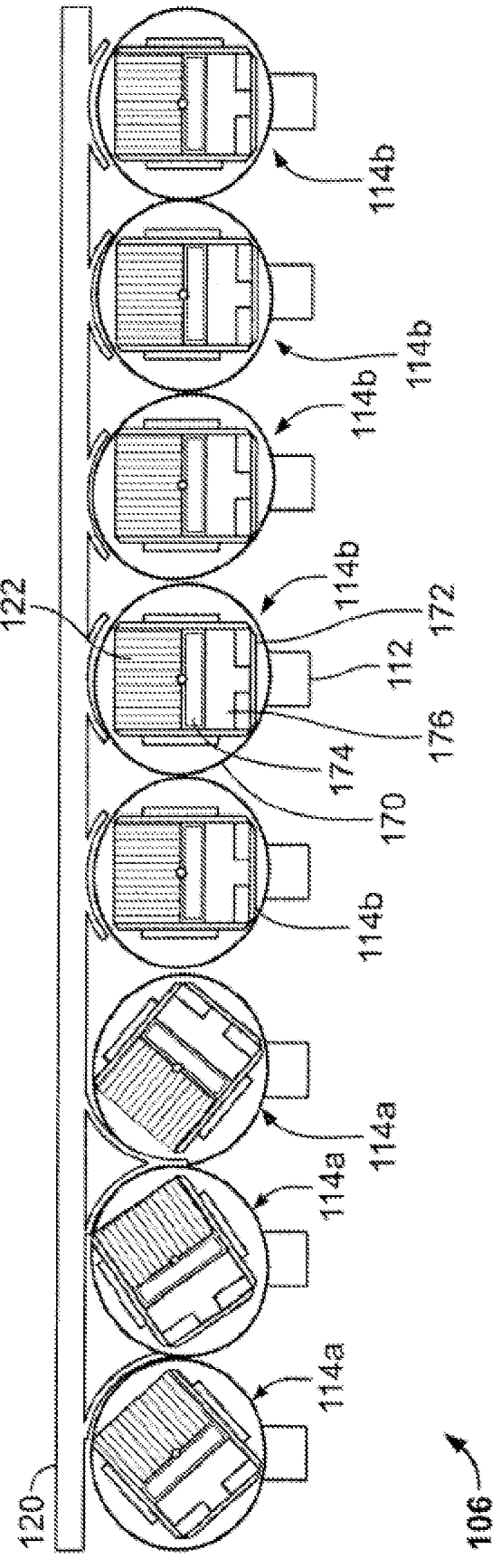
FIG. 1B is a schematic block diagram illustrating detector units, in accordance with an embodiment.
Figure 2A:
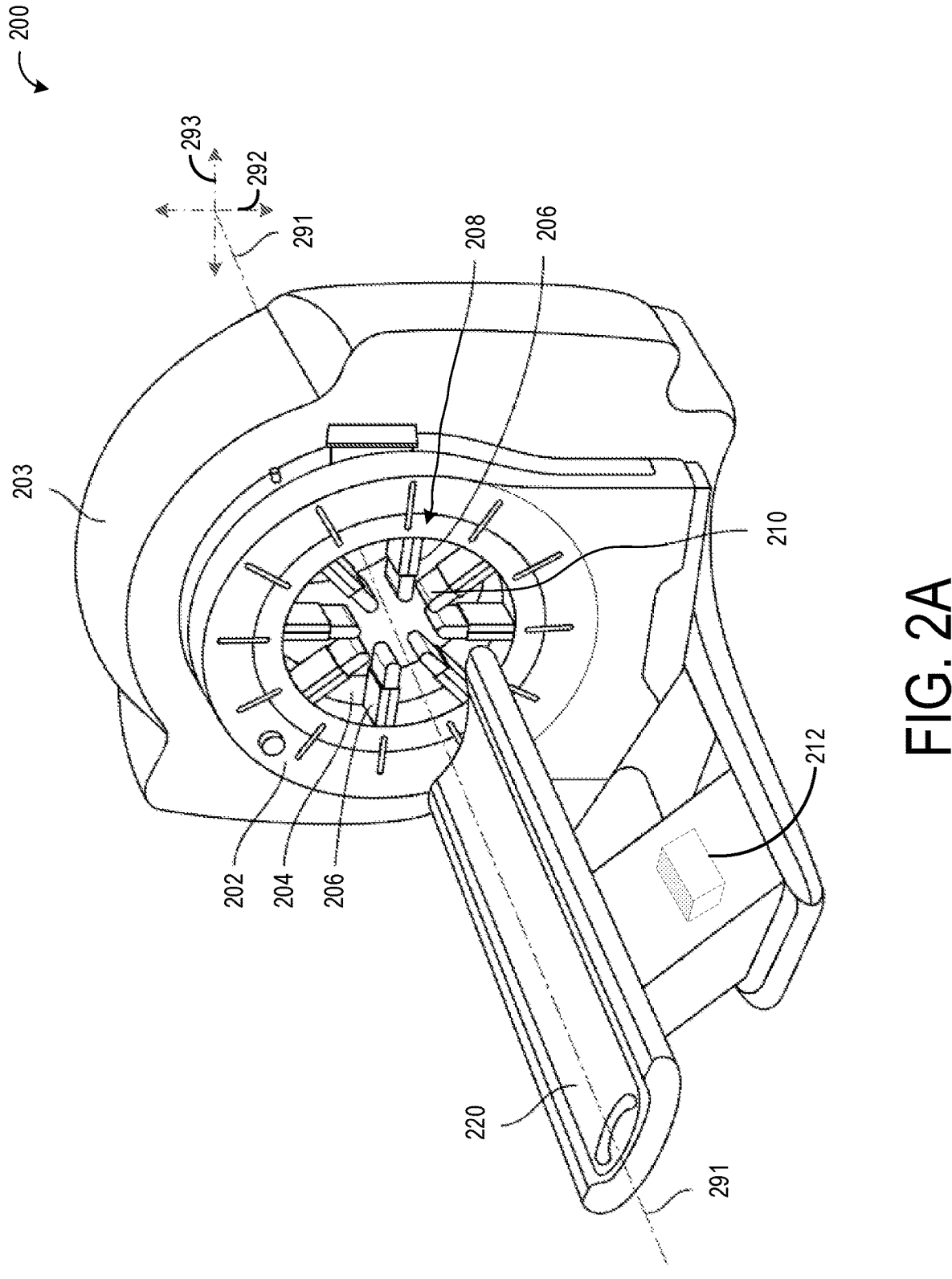
FIG. 2A shows a pictorial view of an exemplary multi-head SPECT imaging system, in accordance with one or more embodiments of the present disclosure.
Figure 2B:
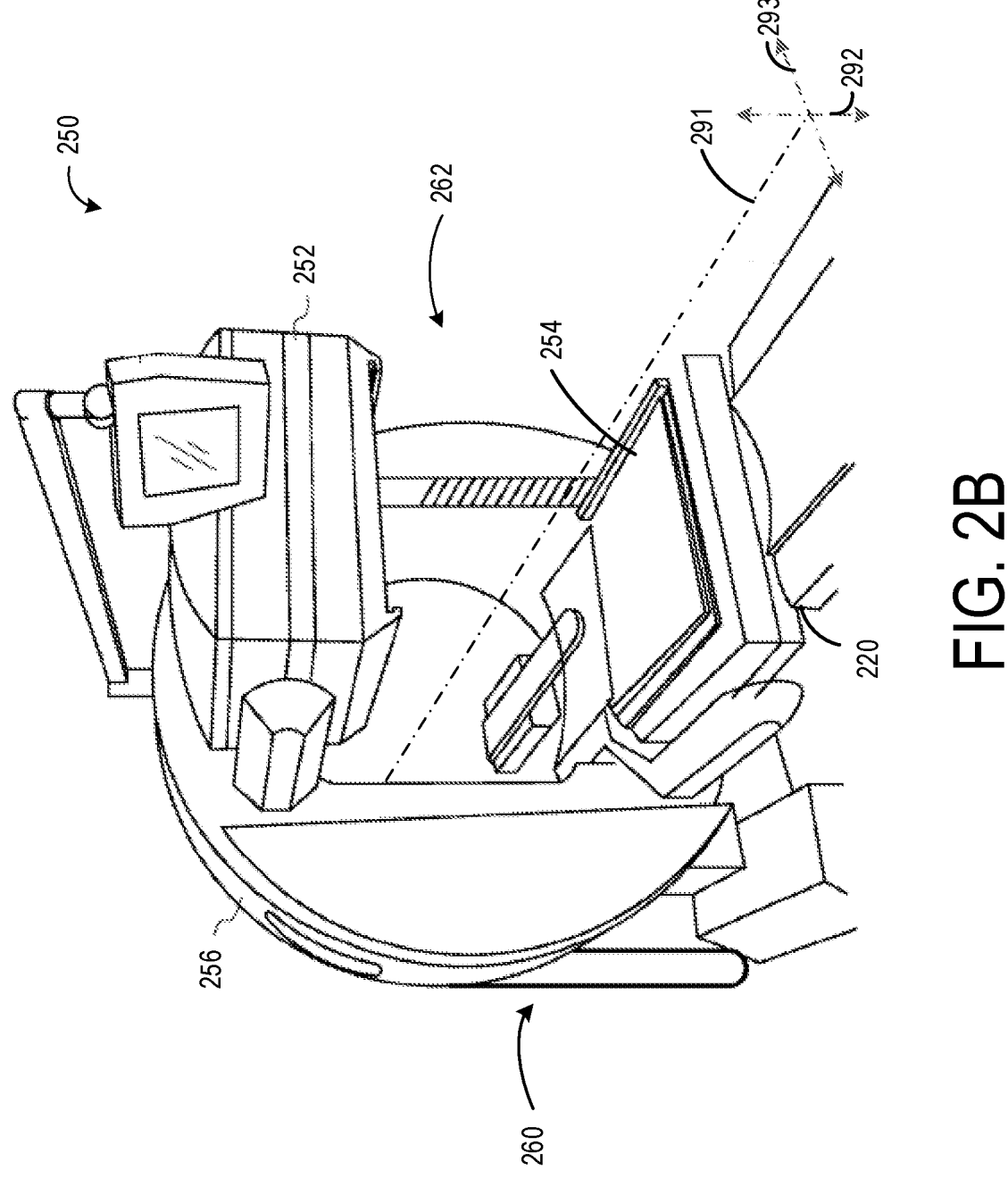
FIG. 2B shows a pictorial view of an exemplary dual-head SPECT imaging system, in accordance with one or more embodiments of the present disclosure.
Figure 3A:
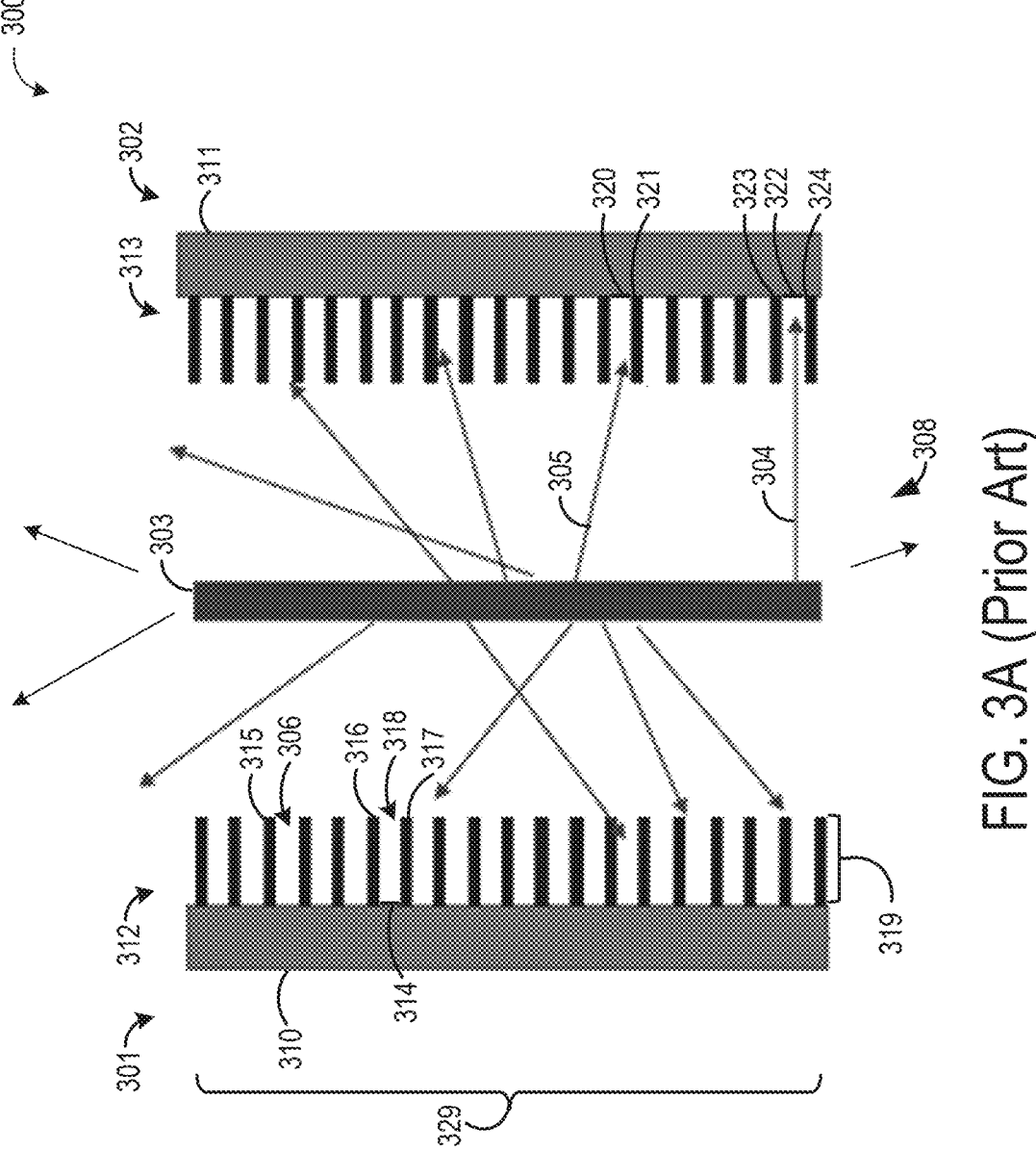
FIG. 3A illustrates an exemplary collimation of radiation from a line source during calibration of a dual-head SPECT system, as prior art.
Figure 3B:
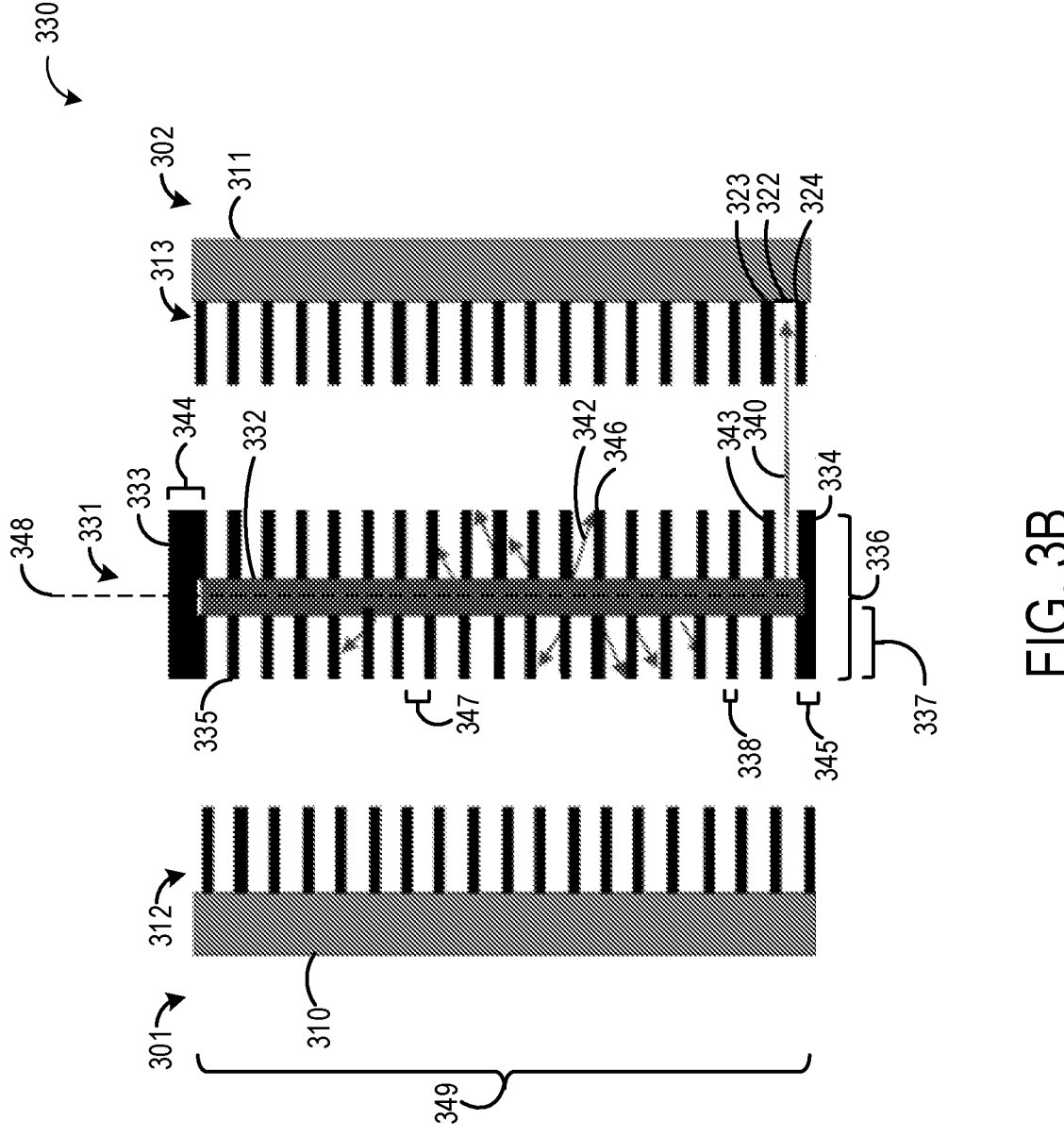
FIG. 3B illustrates a proposed collimated line source for collimating radiation during calibration of the dual-head SPECT system, in accordance with one or more embodiments of the present disclosure.
Figure 4A:
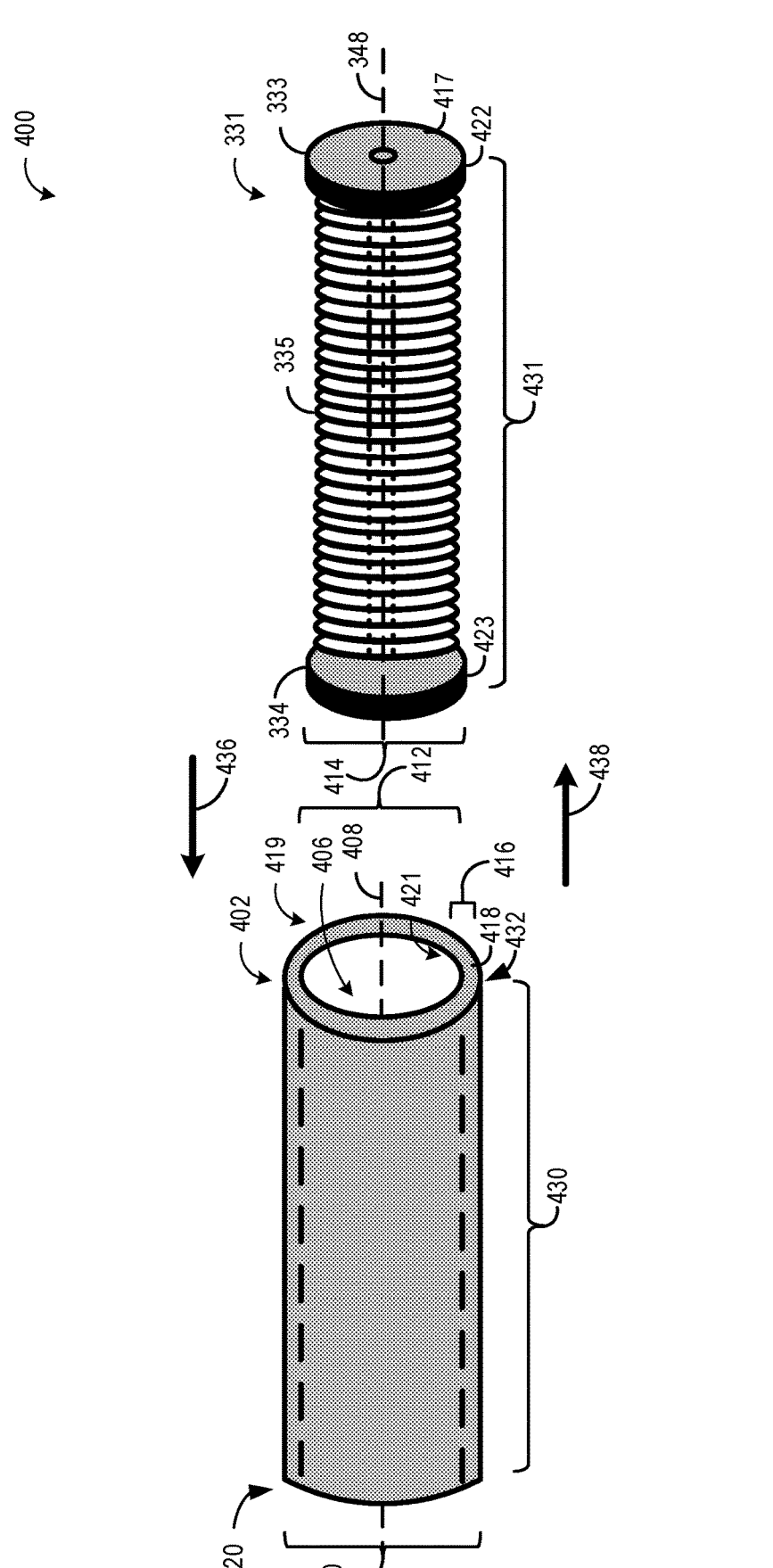
FIG. 4A shows an external shielding of a collimated line source in a first configuration, in accordance with one or more embodiments of the present disclosure.
Figure 4B:
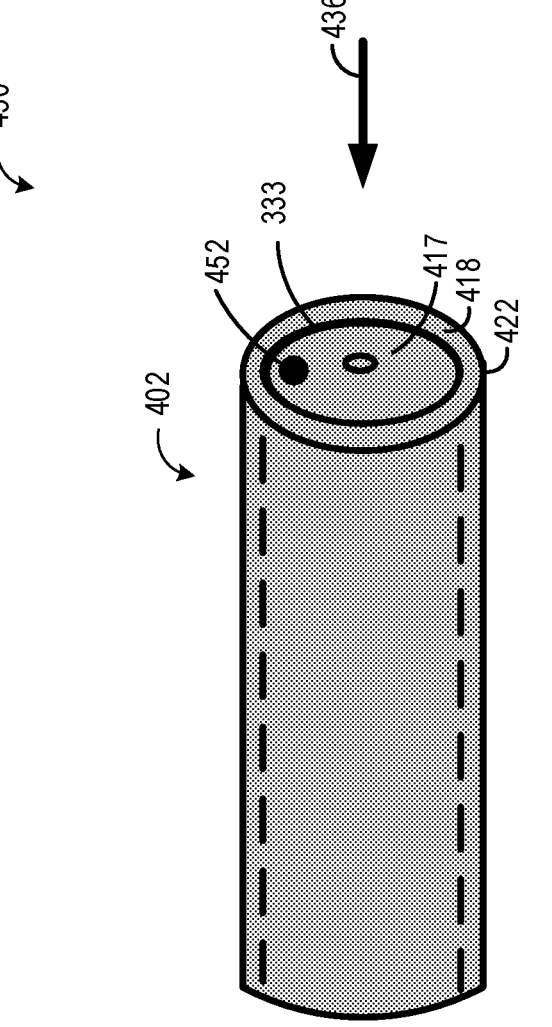
FIG. 4B shows the external shielding of a collimated line source in a second configuration, in accordance with one or more embodiments of the present disclosure.
Figure 4C:
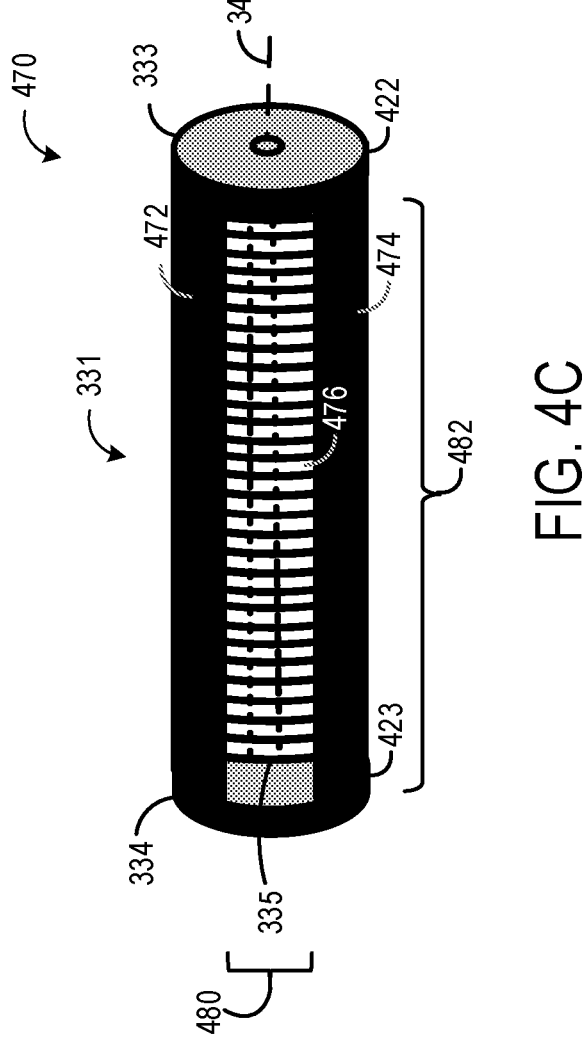
FIG. 4C shows the external shielding of a collimated line source in a third configuration, in accordance with one or more embodiments of the present disclosure.
Figure 5:
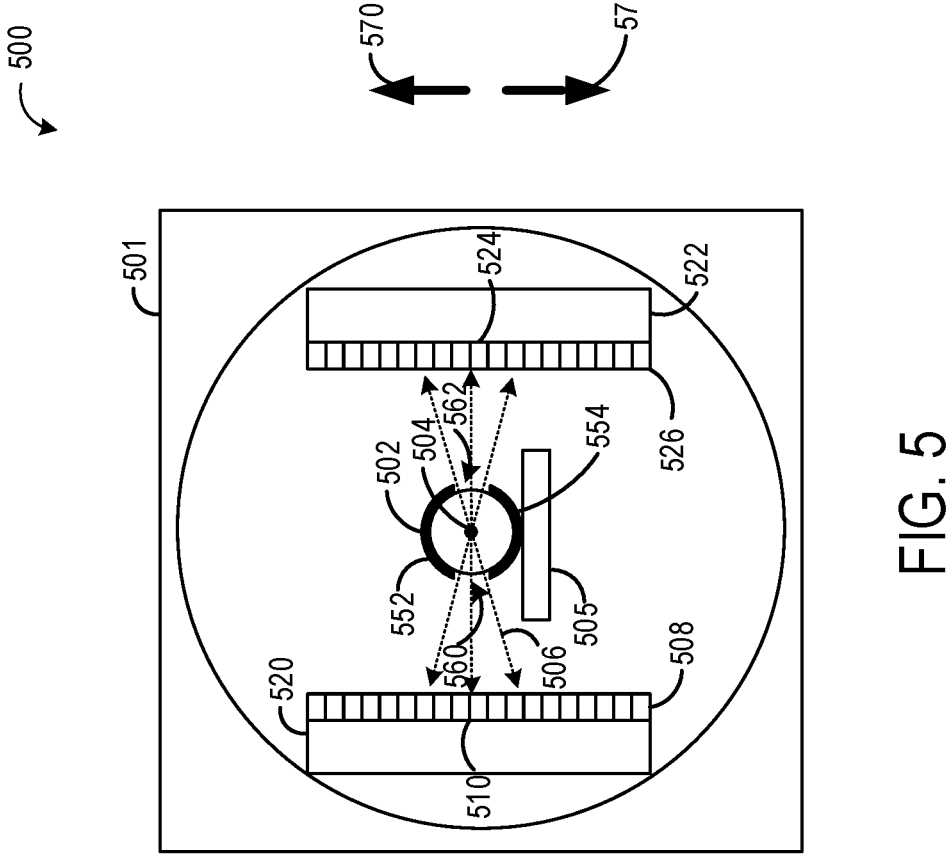
FIG. 5 shows radiation emitting from a collimated line source with a shielding configuration, in accordance with one or more embodiments of the present disclosure.
Figure 6:
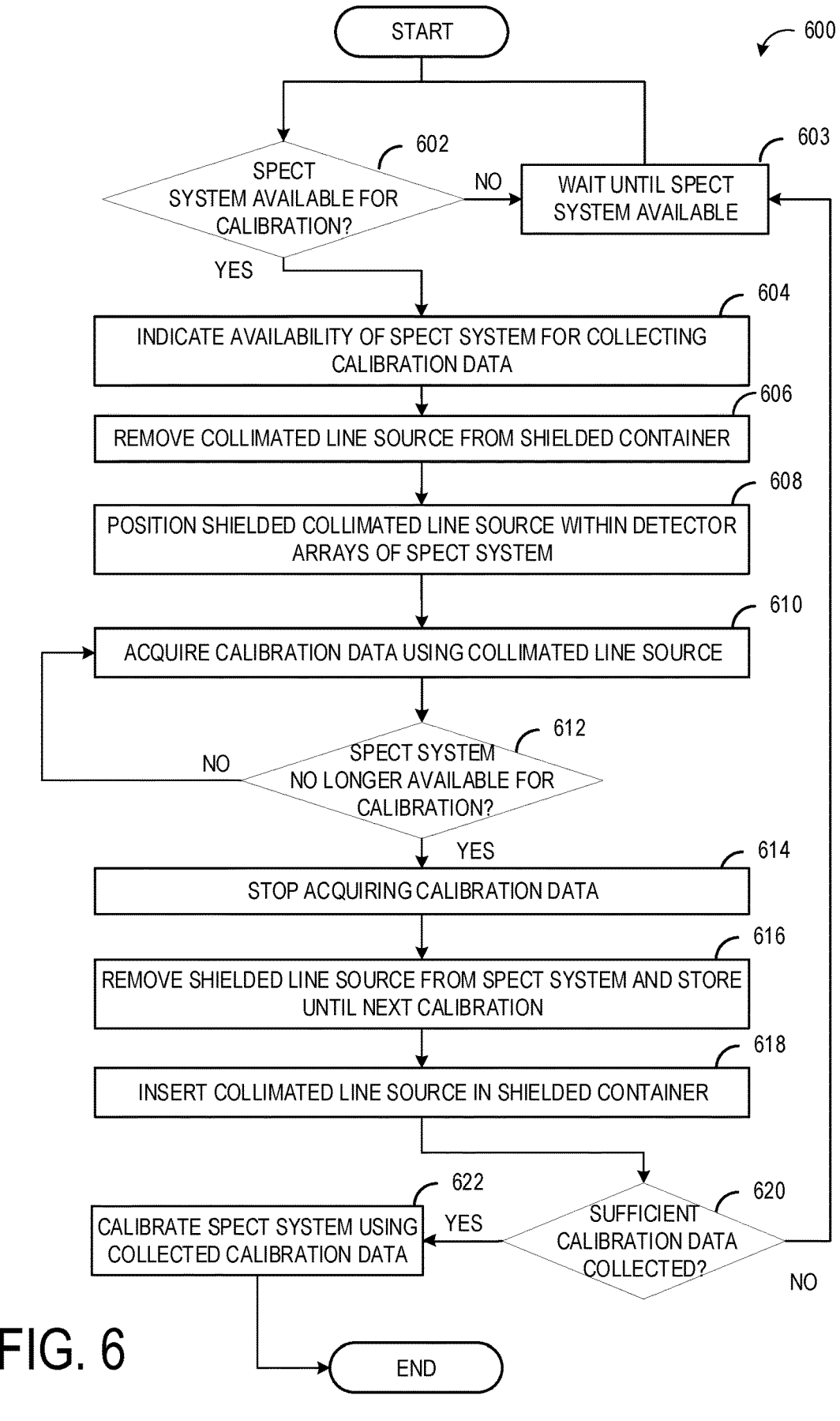
FIG. 6 is an exemplary method illustrating a procedure for calibrating a SPECT system using a collimated line source, in accordance with one or more embodiments of the present disclosure.
Figure 7A:
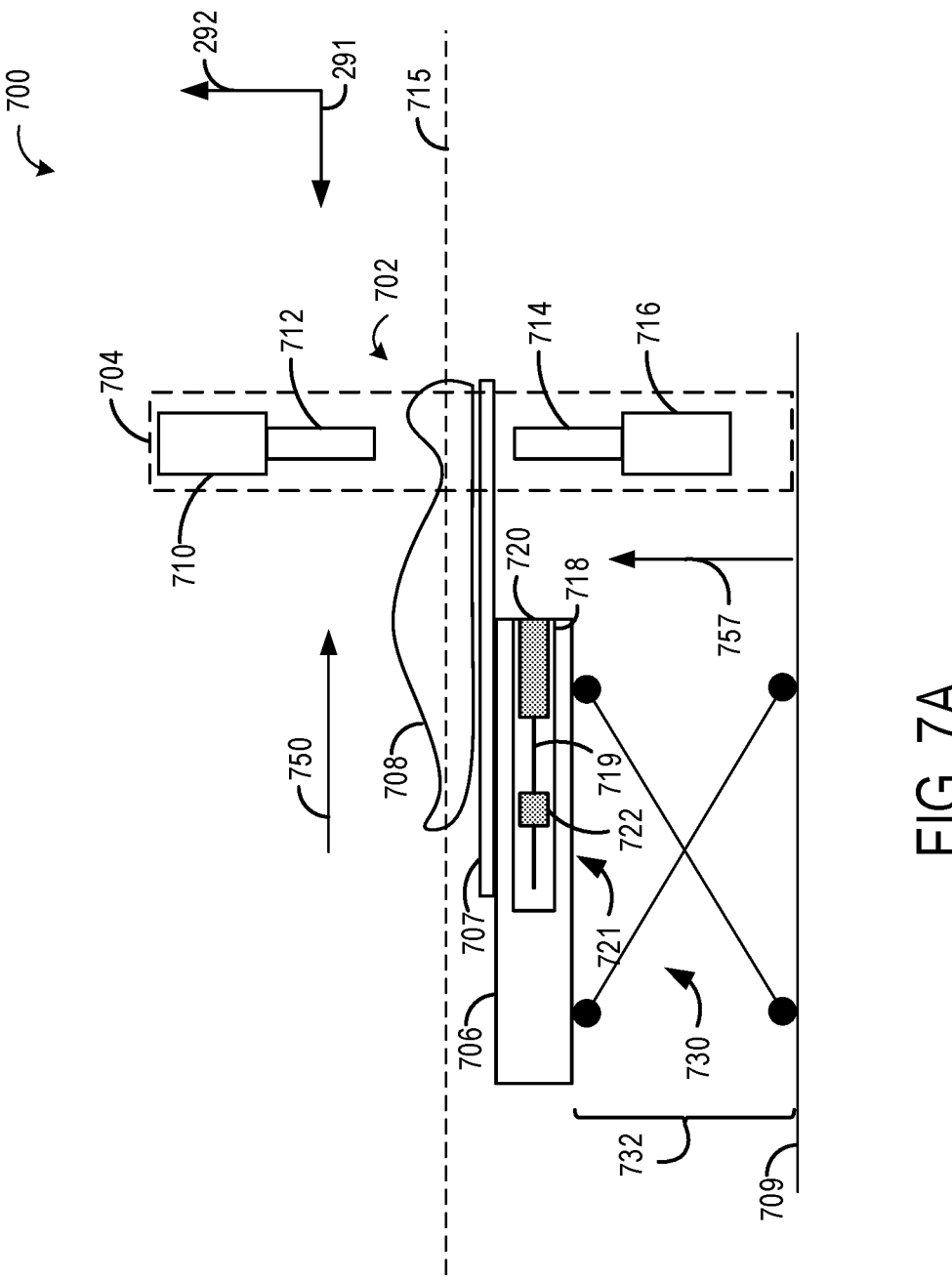
FIG. 7A shows an exemplary configuration of a SPECT system including a retractable collimated line source, in accordance with one or more embodiments of the present disclosure.
Figure 7B:
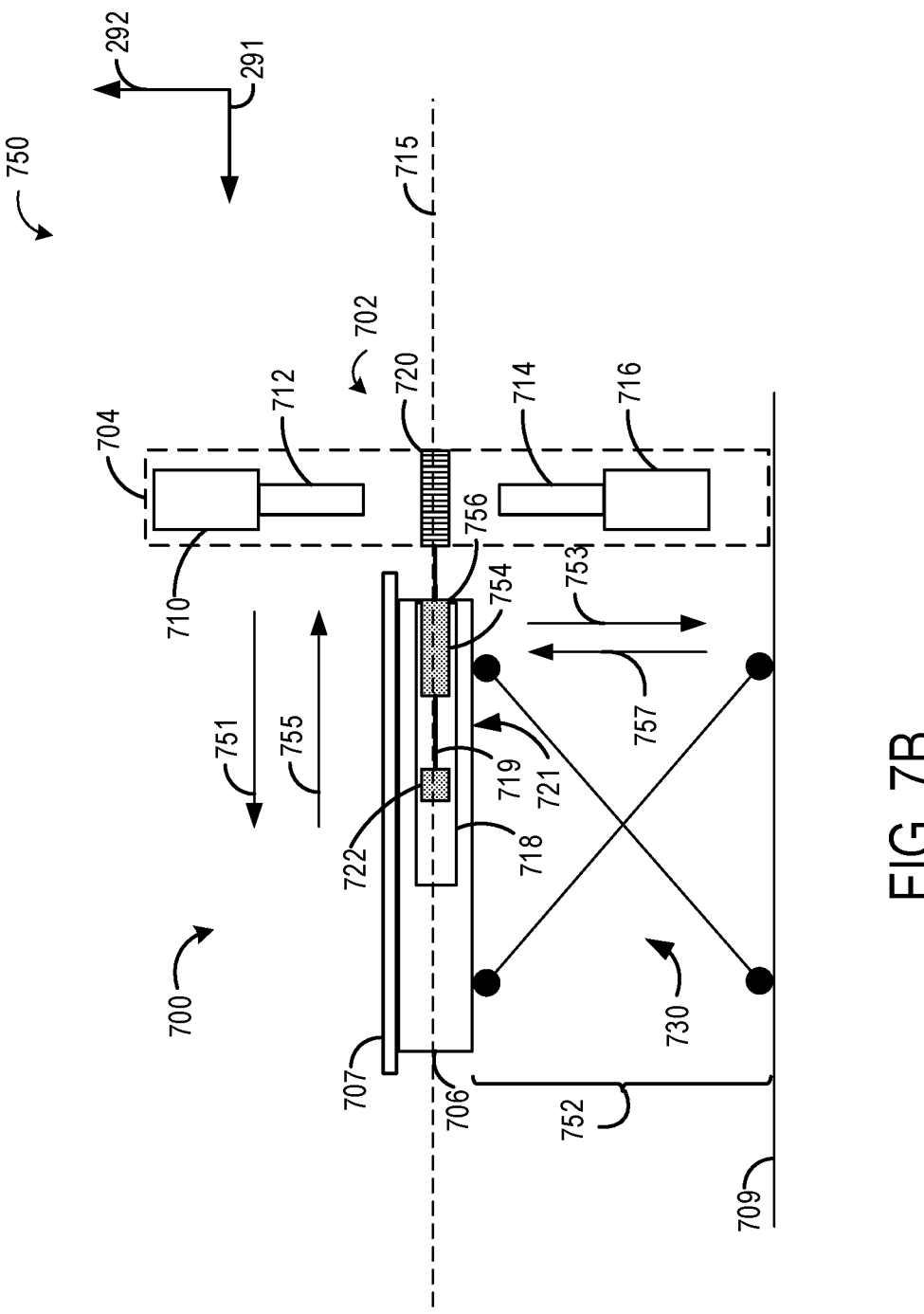
FIG. 7B shows the exemplary configuration of FIG. 7A during calibration of the SPECT system with the retractable collimated line source, in accordance with one or more embodiments of the present disclosure.

An exemplary SPECT system is shown in FIG. 1A, which may include a plurality of detector heads shown in FIG. 1B. FIG. 2A shows a pictorial view of the multi-head SPECT imaging system shown in FIG. 1A. FIG. 2B shows a pictorial view of an alternative, dual-head configuration of the SPECT imaging system. During calibration of the SPECT system, a line source is typically positioned between collimated detector arrays of the SPECT system, as shown in FIG. 3A. An alternative collimated line source that may be used in a dual-head SPECT system is shown in FIG. 3B. The collimated line source may also be used in the multi-head SPECT system of FIG. 3C. FIG. 3D shows a positioning of the collimated line source with respect to a detector array of the multi-head SPECT system. When the collimated line source is not being used for calibration of the SPECT system, the collimated line source may be stored within a container including protective shielding, as shown in FIG. 4B. The collimated line source may be removed from the container for calibrating the SPECT system, as shown in FIG. 4A. The collimated line source may include additional shielding on portions of sides of the collimated line source, as shown in FIG. 4C. During calibration of a dual-head SPECT system, the additional shielding may be used to prevent radiation from being emitted in directions where photons do not impinge on detector arrays, to reduce an amount of radiation released into a room of the SPECT system, as shown in FIG. 5. A method for calibrating the SPECT system using the collimated line source is shown in FIG. 6. When a calibration of the SPECT system is not being performed, the collimated line source may be stored in a bed of the SPECT system, as shown in FIG. 7A. During calibration, the collimated line source may be extracted from the stored location and positioned within the detector heads, as shown in FIG. 7B.

FIG. 1A is a schematic illustration of a NM imaging system 100 having a plurality of imaging detectors mounted on a gantry. The imaging detectors may be configured to rotate around a fixed pivot. The movement of the imaging detectors is controlled to reduce the likelihood or avoid collision among the moving imaging detectors and/or reduce the likelihood of one imaging detector obstructing the field of view of another imaging detector. For example, the NM imaging system in some embodiments provides coordinated swinging or rotating motion of a plurality of imaging detectors or detector heads.

In particular, a plurality of imaging detectors 102 are mounted to a gantry 104 and/or a patient support structure (not shown) (e.g., under a patient table 120), which may define a table support for a patient table 120. In the illustrated embodiment, the imaging detectors 102 are configured as a detector array 106 positioned around the subject 110 (e.g., a patient), as viewed in FIG. 1A. The detector array 106 may be coupled directly to the gantry 104, or may be coupled via support members 112 thereto, to allow movement of the entire array 106 relative to the gantry 104 (e.g., rotational movement in the clockwise or counterclockwise direction as viewed in FIG. 1A). Additionally, each of the imaging detectors 102 includes a detector unit 114, at least some of which are mounted to a movable detector carrier 116 (e.g., a support arm or actuator that may be driven by a motor to cause movement thereof) that extends from the gantry 104. In some embodiments, the detector carriers 116 allow movement of the detector units 114 towards and away from the subject 110, such as linearly. Thus, in the illustrated embodiment the detector array 106 is around the subject 110 and may allow linear movement of the detector units 114, such as towards or away from the patient table 120 in one embodiment. However, other configurations and orientations are possible as described herein, as well as different types of movements (e.g., transverse or perpendicular movement relative to the patient table 120). It should be noted that the movable detector carrier 116 may be any type of support that allows movement of the detector units 114 relative to the support member 112 and/or gantry 104, which in various embodiments allows the detector units 114 to move linearly towards and away from the support member 112, such as radially inward and outwards for positioning adjacent the subject 110. For example, as described herein, the detector units 114 may be controlled to move independently of each other towards or away from the subject 110, as well as capable of rotational, pivoting, or tilting movement in some embodiments.

Each of the imaging detectors 102 in various embodiments is smaller than a conventional whole body or general purpose imaging detector. A conventional imaging detector may be large enough to image most or all of a width of a patient's body at one time and may have a diameter of approximately 50 cm or more. In contrast, each of the imaging detectors 102 may include one or more detector units 114 coupled to a respective detector carrier 116 and having dimensions of 4 cm to 20 cm and may be formed of Cadmium Zinc Telluride (CZT) tiles or modules. For example, each of the detector units 114 may be 8×8 cm in size and be composed of a plurality of CZT pixelated modules (not shown). For example, each module may be 4×4 cm in size and have 16×16=256 pixels. In some embodiments, each detector unit 114 includes a plurality of modules, such as an array of 1×7 modules. However, different configurations and array sizes are contemplated including, for example, detector units 114 having multiple rows of modules.

It should be understood that the imaging detectors may be different sizes and/or shapes with respect to each other, such as square, rectangular, circular, or another shape. An actual field of view (FOV) of each of the imaging detectors 102 may be directly proportional to the size and shape of the respective imaging detector.

The gantry 104 may be formed with an aperture 118 (e.g., opening or bore) therethrough as illustrated. The patient table 120 is configured with a support mechanism, such as the patient support structure, to support and carry the subject 110 in one or more of a plurality of viewing positions within the aperture 118 and relative to the imaging detectors 102. Alternatively, the gantry 104 may comprise a plurality of gantry segments (not shown), each of which may independently move a support member 112 or one or more of the imaging detectors 102.

The gantry 104 may also be configured in other shapes, such as a "C", "H", and "L", for example, and may be rotatable about the subject 110. For example, the gantry 104 may be formed as a closed ring or circle, or as an open arc or arch which allows the subject 110 to be easily accessed while imaging and facilitates loading and unloading of the subject 110, as well as reducing claustrophobia in some subjects 110. For example, in some embodiments the gantry 104 may be arc shaped and the support members 112 movable along the arc to position the detector units 114 at different locations along the gantry 104. In some embodiments, the detector units 114 may also be independently movable along the gantry 104. For example, in some embodiments, NM imaging system 100 may be configured in an alternate dual-head configuration including two detector arrays, each including a set of detector units 114. The two detector arrays may be positioned on opposite sides of an open-arch gantry 104, as described below in reference to FIG. 2B.

Additional imaging detectors (not shown) may be positioned to form rows of detector arrays or an arc or ring around the subject 110. By positioning multiple imaging detectors 102 at multiple positions with respect to the subject 110, such as along an imaging axis (e.g., head to toe direction of the subject 110), image data specific for a larger FOV may be acquired more quickly.

Each of the imaging detectors 102 has a radiation detection face, which is directed towards the subject 110 or a region of interest within the subject 110. The radiation detection faces may be covered by or have coupled thereto a collimator 122. The actual FOV for each of the imaging detectors 102 may be increased, decreased, or relatively unchanged by the type of collimator 122. In one embodiment, the collimator 122 is a multi-bore collimator, such as a parallel-hole collimator. However, other types of collimators, such as converging or diverging collimators may optionally or alternatively be used. Other examples for the collimator 122 include pinhole, parallel-beam converging, diverging fan-beam, converging or diverging cone-beam, multi-bore converging, multi-bore converging fan-beam, multi-bore converging cone-beam, multi-bore diverging, or other types of collimators.

Optionally, multi-bore collimators may be constructed to be registered with pixels of the detector units 114, which in one embodiment are CZT detectors. However, other materials may be used. Registered collimation may increase spatial resolution by forcing photons going through one bore to be collected primarily by one pixel. Additionally, registered collimation may increase sensitivity and energy response of pixelated detectors as detector area near the edges of a pixel or in between two adjacent pixels may have reduced sensitivity or decreased energy resolution or other performance degradation. Having collimator septa directly above the edges of pixels reduces the chance of a photon impinging at these degraded performance locations, without decreasing the overall probability of a photon passing through the collimator.

A controller unit 130 may control the movement and positioning of the patient table 120, imaging detectors 102, gantry 104, and/or the collimators 122. A range of motion before or during an acquisition, or between different image acquisitions, is set to maintain the actual FOV of each of the imaging detectors 102 directed, for example, towards or "aimed at" a particular area or region of the subject 110 or along the entire subject 110.

The controller unit 130 may have a gantry motor controller 132, table controller 134, detector controller 136, pivot controller 138, and collimator controller 140. The controllers 130, 132, 134, 136, 138, 140 may be automatically commanded by a processing unit 150, manually controlled by an operator, or a combination thereof. The gantry motor controller 132 may move the imaging detectors 102 with respect to the subject 110, for example, individually, in segments or subsets, or simultaneously in a fixed relationship to one another. For example, in some embodiments, the gantry controller 132 may cause the imaging detectors 102 and/or one or more of the support members 112 to rotate about the subject 110, which may include motion of less than or up to 180 degrees (or more).

The table controller 134 may move the patient table 120 to position the subject 110 relative to the imaging detectors 102. The patient table 120 may be moved in up-down directions, in-out directions, and right-left directions, for example. The detector controller 136 may control movement of each of the imaging detectors 102 to move closer to and farther from a surface of the subject 110, such as by controlling translating movement of the detector carriers 116 linearly towards or away from the subject 110 (e.g., sliding or telescoping movement). Optionally, the detector controller 136 may control movement of the detector carriers 116 to allow coordinated movement of the detector array 106.

The pivot controller 138 may control pivoting, rotating, or swinging movement of the detector units 114 at ends of the detector carriers 116, and/or the detector carrier 116. For example, one or more of the detector units 114 or detector carriers 116 may be rotated or swung about at least one axis to view the subject 110 from a plurality of angular orientations. The collimator controller 140 may adjust a position of an adjustable collimator, such as a collimator with adjustable strips (or vanes) or adjustable pinhole(s).

It should be noted that motion of one or more imaging detectors 102 may be in directions other than strictly axially or radially, and optionally, motions in several motion directions may be used. Moreover, the motions of the imaging detectors 102 are coordinated in various embodiments as described herein. Therefore, the term "motion controller" may be used to indicate a collective name for all motion controllers. It should be noted that the various controllers may be combined, for example, the detector controller 136 and pivot controller 138 may be combined to provide the different movements described herein.

Prior to acquiring an image of the subject 110 or a portion of the subject 110, the imaging detectors 102, gantry 104, patient table 120, and/or collimators 122 may be adjusted as discussed in more detail herein, such as to first or initial imaging positions, as well as subsequent imaging positions. The imaging detectors 102 may each be positioned to image a portion of the subject 110. Alternatively, one or more of the imaging detectors 102 may not be used to acquire data, such as the imaging detectors 102 at ends of the detector array 106, which as illustrated in FIG. 1A are in a protracted position towards the subject 110. Positioning may be accomplished manually by the operator and/or automatically, which may include using other images acquired before the current acquisition, such as by another imaging modality such as CT. MRI. X-ray, PET, or ultrasound. Additionally, the detector units 114 may be configured to acquire non-NM data, such as x-ray CT data.

After the imaging detectors 102, gantry 104, patient table 120, and/or collimators 122 are positioned, one or more images are acquired by one or more of the imaging detectors 102 being used, which may include pivoting or swinging motion of one or more of the detector units 114, which may pivot, rotate, or swing to different degrees or between different ranges of angles. The image data acquired by each imaging detector 102 may be combined and reconstructed into a composite image, which may comprise two-dimensional (2D) images, a three-dimensional (3D) volume, or a 3D volume over time (4D).

In one embodiment, the imaging detectors 102, gantry 104, patient table 120, and/or collimators 122 remain stationary after being initially positioned. In another embodiment, an effective field of view for one or more of the imaging detectors may be increased by movement such as pivoting, rotating, or swinging one or more of the imaging detectors 102, rotating the detector array 106 with the gantry 104, adjusting one or more of the collimators 122, or moving the patient table 120.

In various embodiments, a data acquisition system (DAS) 160 receives electrical signal data produced by the imaging detectors 102 and converts this data into digital signals for subsequent processing. An image reconstruction device 162 and a data storage device 164 may be provided in addition to the processing unit 150. It should be noted that one or more functions related to one or more of data acquisition, motion control, data processing, and image reconstruction may be accomplished through hardware, software, and/or by shared processing resources, which may be located within or near the imaging system 100, or may be located remotely. Additionally, a user input device 166 may be provided to receive user inputs (e.g., control commands), as well as a display 168 for displaying images.

Additionally, a detector position controller 165 is also provided, which may be implemented in hardware, software, or a combination thereof. For example, as shown in FIG. 1A, the detector position controller 165 may form part of or operate in connection with the processing unit 150. In some embodiments, the detector position controller 165 may be a module that operates to control the movement of the imaging detectors 102, including the detector units 114, such that coordinated or synchronized movement is provided as described herein. It should be noted that movement of a plurality of the imaging detectors 102 and/or detector units 114 may be performed at the same time (e.g., simultaneously or concurrently) or at different times (e.g., sequentially or step-wise, such as back and forth between two detector units 114). It also should be understood that when referring to a detector head, such a detector head may include one or multiple detector modules.

In operation, and as shown, for example, in FIG. 1B, one embodiment includes the detector array 106 positioned (e.g., mounted) under the patient table 120. As can be seen, a plurality of detector units 114*a*, 114*b* are positioned in adjacent arrangement, for example, along one or more rows under the patient table 120 (it should be noted that only a single row of detector units is shown). The detector units in some embodiments are aligned along one or more axes generally perpendicular to the longitudinal axis of the patient table 120, which defines an examination axis (e.g., from head to toe of the subject 110). However, it should be appreciated that the detector units may be aligned in different configurations and orientations, which may be offset from each other, transverse to the longitudinal axis of the patient table 120 and/or parallel to the longitudinal axis of the patient table 120. The detector units illustrated in FIG. 1B may each be non-limiting examples of detector unit 114 of FIG. 1A. Further, detector units 114*a* illustrated in FIG. 1B are arranged at an angle relative to a longitudinal axis of the detector units (which is perpendicular to a longitudinal axis of the patient table) and detector units 114*b* illustrated in FIG. 1B are arranged parallel to the longitudinal axis of the detector units.

As can be seen in the illustrated embodiment, each of the detector units 114*a*, 114*b* includes a housing 170, which are illustrated as circular. However, the housing 170 of the detector units 114*a*. 114*b* may have different shapes and sizes, for example, oval, other curved shapes, etc. The detector units 114*a*, 114*b* include within the housing 170 a detector support 172, which may be a frame or other support structure. A detector 174 is coupled to the detector support 172. For example, the detector 174 may include one or more CZT tiles or modules as described herein, which are connected to electronics 176 (e.g., output electronics to output detected events) therein. Additionally, the collimator 122 is mounted to a front detecting surface of the detector 174. Thus, the detector support 172 is sized and shaped, such as having a base and/or walls, to support and maintain the components of the detector unit 114*a*, 114*b* within the housing 170. For example, the components of the detector unit 114*a*. 114*b* are maintained within the housing 170 when the housing rotates, pivots, or swings as described in more detail herein. In the illustrated embodiment, the detector units 114*a* are shown in a rotated, pivoted, or swung position, while the detector units 114*b* are shown in a non-rotated, non-pivoted, or non-swung position. As can be seen, in the non-rotated, non-pivoted, or non-swung position, the detecting face of the detector is generally parallel to the patient support surface of the patient table 120, while in the rotated, pivoted, or swung position, the detecting face of the detector is not parallel to the patient support surface of the patient table 120. Various embodiments provide coordinated or synchronized movement of the detector units 114*a*, 114*b*, which allows the detector units 114*a*, 114*b* to be positioned or packed in closer alignment than in conventional systems. For example, in some embodiments, different detector units 114*a*, 114*b*, such as adjacent detector units 114 may move along different angular ranges, to a different angular position, and/or at different velocities.

It should be noted that the arrangement of detector units 114 in the detector array 106 may be provided in other portions of the NM imaging system 100, such as at positions along the gantry 104 or as part of the detector array 106. Also, it should be noted that in some embodiments, a housing 170 is not provided surrounding or encasing the components within the detector units 114.

As seen in FIG. 1B, the housings 170 for detector units 114 are generally circular in shape and lie in close proximity to each other. As such, rotation of each detector unit 114 about its individual axis does not physically interfere with the adjacent detector units. The circular housings 170 allow for a small clearance in between each detector unit 114 to allow for complete rotation of each detector unit during operation of NM imaging system 100.

FIG. 2A is a perspective view of a nuclear medicine (NM) imaging system 200. The NM imaging system 200 includes elements that are similar or identical to the elements of the NM imaging system 100. It should be noted that the arrangement of FIG. 2A is provided by way of example for illustrative purposes, and that other arrangements may be employed in various embodiments. The NM imaging system 200 of FIG. 2A is configured as a SPECT imaging system. In the illustrated embodiment, the NM imaging system 200 has a gantry 202 including a cavity 204 that is sized and shaped to receive an object therein. In particular embodiments, the object is a patient (e.g., human or animal). The cavity 204 is oriented relative to mutually perpendicular longitudinal, vertical, and horizontal axes 291, 292, 293. The cavity 204 extends lengthwise along the longitudinal axis 291. In the illustrated embodiment, the longitudinal axis 291 is a central longitudinal axis that extends through a geometric center of the cavity 204. The vertical axis 292 extends parallel to a gravitational force in FIG. 2A. However, for other configurations of the NM imaging system, the vertical axis 292 may not extend parallel to the gravitational force. Optionally, the NM imaging system 100 may adjoin or be positioned adjacent to a computed tomography (CT) imaging system (not shown). The gantry 202 has a discrete housing 203 and is configured to rotate at a rotational speed in one or both directions about the longitudinal axis 291.

The NM imaging system 200 also includes a plurality of detector assemblies 206 (e.g., detector units 114 of FIGS. 1A and 1B). As shown, the detector assemblies 206 are positioned in an array 208 in which the detector assemblies 206 are distributed at least partially around the cavity 204. In the illustrated embodiment, the detector assemblies 206 are evenly distributed circumferentially about the longitudinal axis 291. Each of the detector assemblies 206 in the array 208 includes a movable arm (not shown) and a detector head 210 that is coupled to the movable arm. The movable arm is configured to move the detector head 210 toward and away from the object within the cavity 204.

Also shown, the NM imaging system 200 includes a movable table 220. The movable table 220 is configured to receive the object (e.g., a patient) and move the object into the cavity 204 along the longitudinal axis 291. In some embodiments, the movable table 220 may move in one or both directions along the vertical axis 292 and in one or both directions along the horizontal axis 293. Movement along the vertical axis 292 and the horizontal axis 293 may occur simultaneously or in separate movements (e.g., first up, then over). As set forth herein, the NM imaging system 200 may move the detector heads 210 and the movable table 220 so that a series of detector heads 210 are positioned in a dense group that borders the object.

The movable table 220 is operably coupled to one or more motors 212 that are controlled by one or more processors (not shown). The motors 212 are configured to move the movable table 220 to a designated position. For example, the processor(s) may control the motors 212 and the detector assemblies 206 so that the object has a desired position relative to the detector heads 210.

FIG. 2B shows an alternate, dual-head configuration 250 of NM imaging system 100. In dual-head configuration 250, a first head 252 includes a first detector array with a first set of detector units (e.g., detector units 114 of FIG. 1A), and a second head 254 includes a second detector array with a second set of detector units. First head 252 and second head 254 may be arranged on a gantry 256 (e.g., gantry 104), which may be an open-arch gantry. As described above in reference to FIG. 1A, gantry 256 may rotate around a subject positioned on a movable table 220 (e.g., movable table 120). In FIG. 2B, first head 252 is aligned horizontally above movable table 220, and second head 254 is aligned horizontally below movable table 220, with respect to vertical axis 292. Alternatively, gantry 256 may be rotated such that first head 252 is aligned vertically at a first side 260 of movable table 220, and second head 254 is aligned vertically at a second, opposite side 262 of movable table 220, with respect to horizontal axis 293. In various embodiments, first head 252 and second head 254 may be aligned vertically during a calibration of NM imaging system 100 using a line source, as described in greater detail below in reference to FIG. 5. An angle between first head 252 and second head 254 may be preferably adjustable between 90 degrees and 180 degrees, using conventional means, and/or a distance between first head 252 and second head 254 may be adjusted and a transverse position of each of first head 252 and second head 254 (or of both together) may be adjusted, using conventional mechanical structures. Additionally, movable table 220 may be adjusted up or down along vertical axis 292, for example, to center a subject between first head 252 and second head 254. First head 252 and second head 254 may also be adjusted up or down along vertical axis 292, for example, to reduce or increase a distance between either or both of first head 252 and second head 254 and the subject.

FIG. 3A shows a first collimation diagram 300 with a side view perspective of an exemplary collimation of radiation photons by a SPECT system during calibration, which may be a non-limiting example of NM imaging system 100 of FIG. 1A. In the depicted embodiment, the SPECT system is a dual-head configuration, such as the dual-head configuration 250 of FIG. 2B. However, it should be appreciated that the description provided herein also applies to multi-head configurations such as the multi-head imaging system 200 of FIG. 2A.

The dual-head SPECT system includes a first head 301 and a second head 302, which may be positioned on opposite sides of a gantry, such as gantry 104, such that a subject may be positioned in a space 308 between first head 301 and second head 302. First head 301 includes a first detector array 310 and a first collimator 312, and second head 302 includes a second detector array 311 and a second collimator 313. Each of first detector array 310 second detector array 311 include a plurality of detector elements (e.g., pixels) arranged facing space 308, such that radioactive particles (e.g., photons) of a radioactive tracer administered to the subject may be detected by detector elements. Each detector element may generate an electrical signal when a photon is detected by the element, and the electrical signals from the plurality of detector elements may be combined to generate a 3D image of a portion of a body of the subject.

In various embodiments, first collimator 312 and second collimator 313 comprise sheets of a material with a high atomic number and a high density that absorbs radioactive particles. For example, the material may be lead, tungsten, molybdenum, or a material with a similar density and atomic number. First collimator 312 and second collimator 313 may be perforated to include a plurality of holes 306 arranged facing space 308, where each hole 306 may be aligned with a detector element of a corresponding detector array. In other words, a first length and first width of each hole 306 may be equal to a second length and second width of the detector element. The plurality of holes 306 may thus create a plurality of collimator septa 315 (e.g., walls) surrounding each detector element, that extend out from the respective detector element towards space 308. For example, first collimator 312 may include a hole 318 aligned with a detector element 314, where a first septa portion 316 and a second septa portion 317 created by hole 318 extend towards space 308. (Although not shown in FIG. 3A, the hole may be a two-dimensional hole blocked on four sides). First septa portion 316 and second septa portion 317 may have a first length 319, equal to a thickness of the sheet of high-density material used for first collimator 312. For example, first length 319 may be 20 mm. It should be appreciated that in FIGS. 3A-3D, a single row of holes 306 is shown in cross-section, where detector arrays 310 and 311 may include a plurality of holes at the locations indicated by arrows in FIGS. 3A-3D, where the plurality of holes correspond to other rows not depicted in this cross-sectional perspective.

During calibration of the dual-head SPECT system, a line source 303 may be positioned in space 308, at a location of the subject. Line source 303 may include a radionuclide, such as, for example, Co-57, that emits a consistent amount of radiation. Specifically, line source 303 may emit a constant amount of radiation photons in all directions (e.g., 360 degrees). The radiated photons are indicated in FIG. 3A by a plurality of arrows.

In first collimation diagram 300, line source 303 has a same length 329 as first head 301 and second head 302. An advantage of line source 303 having the same length 329 as first head 301 and second head 302 is that during a calibration, all detector elements of first head 301 and second head 302 may detect photons of line source 303 without having to adjust a position of line source 303. In other words, if line source 303 were shorter than length 329, performing the calibration may include moving line source 303 to expose all the detector elements to photons of line source 303. In one embodiment, the length of line source 303 may be 320 mm.

Photons directed at first collimator 312 and second collimator 313 at or near a perpendicular angle may be detected by detector elements of first detector array 310 and second detector array 311, respectively. However, a majority of the radiated photons not be directed at first collimator 312 and second collimator 313 at or near the perpendicular angle. Photons striking the septa of first collimator 312 and second collimator 313 may be absorbed, and may not be detected at the detector elements.

For example, a first photon 304 may be directed at second detector array 311 at or near the perpendicular angle, whereby first photon 304 may not strike surrounding septa (e.g., where portions 323 and 324 of the septa are visible in the perspective view of FIG. 3A). As a result of not striking the septa, first photon 304 may be detected by a detector element 322 of second detector array 311. In contrast, a second photon 305 may be directed at second detector array 311 at a different, non-perpendicular angle, whereby second photon 305 may strike a portion 321 of the surrounding septa. As a result of striking the septa, second photon 305 may be absorbed by the material of the septa, and second photon 305 may not be detected by a detector element 320 of second detector array 311.

Thus, the septa of first collimator 312 and second collimator 313 are configured to allow photons emitted by line source 303 at the perpendicular angle to be detected by first detector array 310 and second detector array 311, respectively, and to prevent photons emitted by line source at other angles from being detected by first detector array 310 and second detector array 311, respectively. Since a number of photons emitted by line source 303 (or the subject) at the perpendicular angle is typically a small fraction of a total number of photons emitted by line source 303, a large amount of radiation is generated that is not useful for calibrating the SPECT system. The large amount of radiation may be released into a room of the SPECT system, subjecting technicians, operators, subjects, and/or other persons present in the room to exposure. Because of the exposure, the technicians, operators, subjects, and/or other persons may have to leave the room during calibration of the SPECT system. As a result of the technicians, operators, subjects, and/or other persons not being able to use the room or the SPECT system during the calibration, the calibration may be performed at a scheduled period of time when the SPECT system is not otherwise in use. The scheduled period of time may be several hours, resulting in a decrease in availability of the SPECT system for examinations, thereby reducing an efficiency of use of the SPECT system. Alternatively, shields may be placed at positions in the room to protect the technicians, operators, subjects, and/or other persons, but the shields may increase a cost of the SPECT system and may not provide adequate protection.

FIG. 3B shows a second collimation diagram 330 where the SPECT system of FIG. 3A is calibrated using an alternative, collimated line source 331. Collimated line source 331 may reduce an amount of scheduled downtime of the SPECT system for calibration, by reducing an amount of radiation to which the technicians, operators, subjects, and/or other persons may be exposed while calibration data is being collected.

Collimated line source 331 has a same length 349 as first head 301 and second head 302. However, it should be appreciated that the length of collimated line source 331 may be smaller or larger than the length of first head 301 and second head 302 without departing from the scope of this disclosure. Length 349 may be the same as or similar to length 329 of FIG. 3A.

Collimated line source 331 includes a line source 332, which may be the same as or similar to line source 303 of FIG. 3A. However, in contrast to line source 303, collimated line source 331 may include a plurality of parallel collimator plates 335 arranged around line source 332. Collimator plates 335 may be constructed out of a same or similar material as first collimator 312 and second collimator 313. In various embodiments, collimated line source 331 may have a cylindrical shape, where each collimator plate 335 may be a flat sheet of the material in a circular, disc shape with a thickness 338 and a diameter 336. For example, thickness 338 may be 0.2 mm, and diameter 336 may be 50 mm. Thus, each collimator plate 335 may extend outward from line source 332 for a distance 337. For example, distance 337 may be 20 mm. In other embodiments, collimated line source 331 may not have a cylindrical shape, and each collimator plate 335 may not have a circular shape, and may have a different shape, such as a square, hexagonal, or other shape. In some embodiments, collimated line source 331 may have a cylindrical portion, and may include one or more flat surfaces and/or stabilizing components positioned on sides of the cylindrical portion to prevent collimated line source 331 from rolling.

Collimator plates 335 may be evenly spaced along a central axis 348 of collimated line source 331, such that each collimator plate 335 is a same distance 347 from a neighboring collimator plate 335. In one example, distance 347 may be 1-3 mm. In some embodiments, distance 347 may be based on a desired plurality of rows of detector elements of the SPECT imaging system that may detect photons emitted by line source 332 between two neighboring collimator plates 335. For example, distance 347 may be equal to a total width of the desired plurality of rows of detector elements of the SPECT imaging system, where each row has an individual width corresponding to a width of a single detector element of detector arrays 310 and 311.

In other embodiments, the collimation of the source may have larger emission angles than acceptance angles of the collimators 312,313 on the first head 301 and second head 302, respectively, to prevent a misalignment from creating reduced detection of the radiation, which may lead to artifacts. This may be achieved by smaller aspect ratio between septa height (e.g., distance 337) over pitch (e.g., distance 347) of the collimation of collimated line source 331.

Thus, photons emitted by line source 332 and passing between two collimator plates 335 may be detected at a corresponding plurality of rows of detector elements of detector arrays 310 and 311 arranged facing collimated line source 331, and may not be detected at other detector elements of detector arrays 310 and 311 not in the corresponding plurality of rows.

Collimated line source 331 additionally includes a first end cap 333 at a first end of collimated line source 331, and a second end cap 334 at a second end of collimated line source 331. First end cap 333 and second end cap 334 may be manufactured from a same material as collimator plates 335. First end cap 333 and second end cap 334 may shield the first end and second end of line source 332, such that radiation emitted by line source 332 may not pass through first end cap 333 and second end cap 334 into an environment where humans may be exposed to the radiation. In other words, first end cap 333 and second end cap 334 may constitute portions of an external shielding of line source 332 used to contain radiation emitted by line source 332 when line source 332 is not in use during calibration, as described in greater detail below in reference to FIGS. 4A and 4B. First end cap 333 has a first thickness 344, and second end cap 334 has a second thickness 345. First thickness 344 and second thickness 345 may be greater than thickness 338 of a single collimator plate 335. First thickness 344 may be equal to second thickness 345, or first thickness 344 may not be equal to second thickness 345. Additionally, in some embodiments, a diameter of first end cap 333 and second end cap 334 may be greater than a diameter of collimator plates 335.

Collimator plates 335 (and end caps 333 and 334) may absorb photons emitted by line source 332 at angles outside of a threshold angle of perpendicular, while allowing photons emitted by line source 332 within the threshold angle of perpendicular to be directed to first detector array 310 or second detector array 311. For example, a first collimated photon 340 may be emitted by line source 332 at a perpendicular angle (e.g., 90 degrees from central axis 348 of line source 332). First collimated photon 340 may pass through a first collimator plate 343 and second end cap 334, and may also pass through the septa (e.g., in the side perspective depicted in FIG. 3B, through the visible portions 323 and 324 of the septa) of second detector array 311, to be detected by a detector element 322, where detector element 322 is in a corresponding row of detector elements aligned with a portion of line source 332 positioned between collimator plate 343 and second end cap 334. In contrast, a second collimated photon 342 may be emitted by the portion of line source 332 at an angle outside the threshold angle of perpendicular. Second collimated photon 342 may be absorbed by a second collimator plate 346, and may not be detected by any detector elements of second detector array 311.

Thus, a majority of photons emitted by line source 331 may be absorbed by collimator plates 335, while a minority of perpendicularly emitted photons may be allowed to pass through collimator plates 335. The perpendicularly emitted photons are directed through the collimating septa of detector arrays positioned around collimated line source 331. Because non-perpendicularly emitted photons of line source 332 would be absorbed by the collimating septa of the detector arrays, collimator plates 335 may not affect a collection of photon count data during a calibration of the dual-head SPECT system. However, by reducing a number of radiation photons escaping collimator plates 335, the amount of radiation emitted by line source 331 into the environment where humans may be exposed may be reduced.

In some embodiments, the source collimator may optionally be constructed by alternating thin "washers" of absorbing material (acting as septa) with thicker, highly radiation transmitting washers (e.g. plastic foam), held together by glue or the central line source, which may make mechanical construction easier.

Figure 3C:
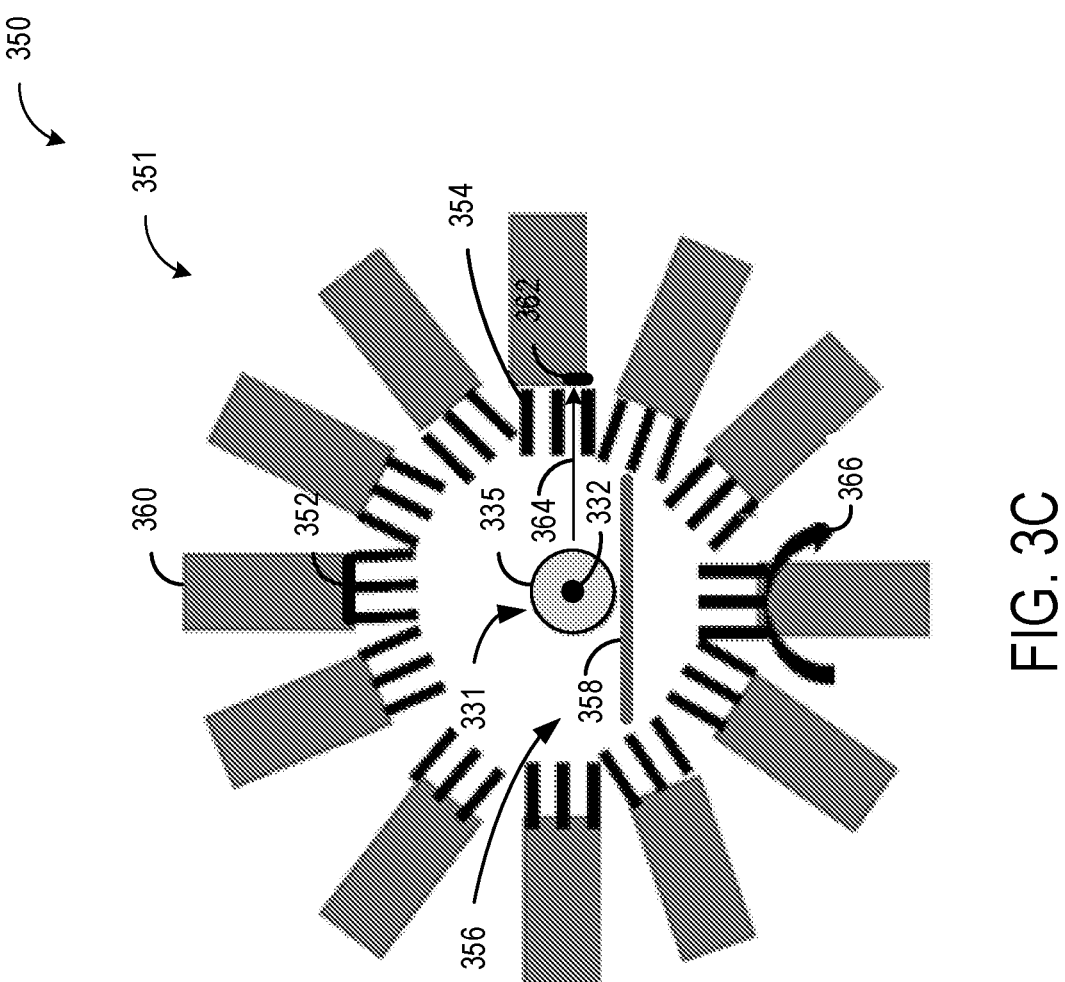
FIG. 3C shows a front view of a collimated line source during calibration of a multi-head SPECT system, in accordance with one or more embodiments of the present disclosure.
Figure 3D:
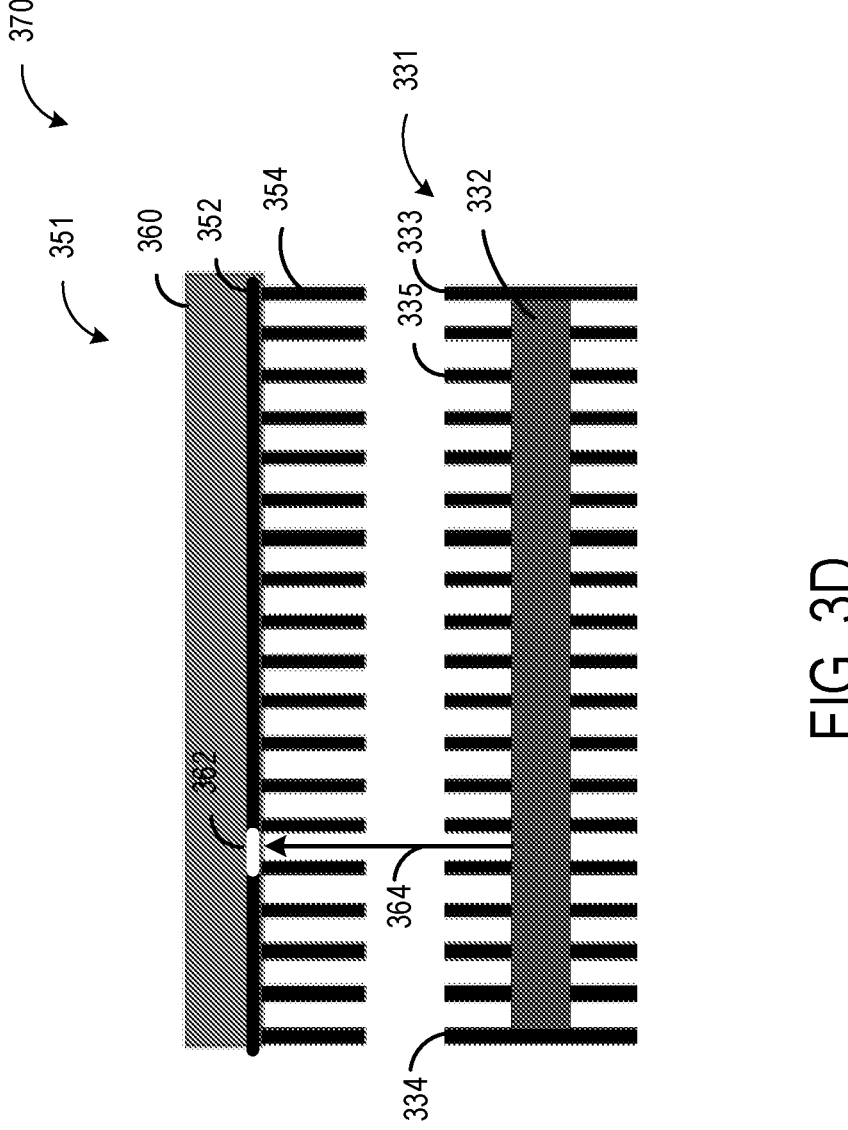
FIG. 3D shows a side view of the collimated line source during calibration of the multi-head SPECT system, in accordance with one or more embodiments of the present disclosure.

FIG. 3C shows a third collimation diagram 350, where collimated line source 331 is used to calibrate a multi-head SPECT system 351. In third collimation diagram 350, a front view of multi-head SPECT system 351 is depicted, where collimated line source 331 is positioned on a table 358 (e.g., table 120 of FIG. 1A) within a space 356 surrounded by a plurality of heads 360 (e.g., detector units 114 of FIG. 1B) of multi-head SPECT system 351. Each head 360 may include a detector array 352 which may include a plurality of detector elements (e.g., pixels). As in FIG. 3B, the detector elements may be collimated via collimator septa 354, similar to septa 315, such that radiation emitted by collimated line source 331 at a perpendicular angles may be detected at the detector elements. For example, a photon directed as shown by an arrow 364 may be detected at a detector array 362 of multi-head SPECT system 351. A sweep of motion of detector arrays 352 around collimated line source 331 is shown by an arrow 366.

FIG. 3D shows a fourth collimation diagram 370, where collimated line source 331 is used to calibrate multi-head SPECT system 351. In fourth collimation diagram 370, a side view of a head 360, detector array 352, and septa 354 of multi-head SPECT system 351 is depicted. Similarly, a side view of collimated line source 331 is depicted, including line source 332, end caps 333 and 334, and collimator plates 335. Fourth collimation diagram 370 shows the photon indicated by arrow 364, which is emitted at the perpendicular angle from collimated line source 331 such that enters septa 354 and is detected at detector array 362.

FIG. 4A shows an unshielded line source diagram 400 including an exemplary shielded container 402 that may be used to store collimated line source 331. When collimated line source 331 is not being used to calibrate a SPECT system such as NM imaging system 100 and/or 200, collimated line source 331 may be stored in shielded container 402 to reduce a probability that humans are exposed to radiation emitted by collimated line source 331. For example, at a time of calibration, collimated line source 331 may be retrieved from a storage location and positioned within the SPECT system, as described above in reference to FIGS. 3A-3D. During transportation of collimated line source 331 from the storage location to the SPECT system, people in a room of the SPECT system may be evacuated to avoid radiation exposure if collimated line source 331 is not properly shielded within shielded container 402.

Like collimator plates 335, shielded container 402 may be manufactured out of a material with a high atomic number and a high density that absorbs radioactive particles, such as lead, tungsten, molybdenum, or a different high-density material.

Shielded container 402 may have a hollow, cylindrical shape with an inner diameter 412, which may be greater than or equal to an outer diameter 414 of end cap 334 of collimated line source 331. In one embodiment, inner diameter 412 is equal to outer diameter 414, and collimated line source 331 may be positioned within an internal space 406 of shielded container 402 such that an outer surface 417 of end cap 333 of collimated line source 331 is flush with an outer surface 418 of a first end 419 of shielded container 402. In other embodiments, collimated line source and/or shielded container 402 may have a different, non-cylindrical shape (e.g., rectangular, etc.) When collimated line source 331 is flush with an outer surface 418, there may be no space between an outer wall 422 of end cap 333 and an inner wall 421 of shielded container 402, and no space between an outer wall 423 of end cap 334 and inner wall 421.

Referring briefly to FIG. 4B, a shielded line source diagram 450 shows collimated line source 331 inserted into shielded container 402, where outer surface 417 of end cap 333 of collimated line source 331 is flush with outer surface 418 of a first end 419 of shielded container 402. In various embodiments, when outer surface 417 is flush with outer surface 418, a locking mechanism of collimated line source 331 may be engaged, which may secure collimated line source 331 within shielded container 402 and prevent collimated line source 331 from accidentally sliding out of shielded container 402. To remove collimated line source 331 from shielded container 402, the locking mechanism may be released. For example, in one embodiment, the locking mechanism may be released manually by a technician or operator of the SPECT system by pressing a button 452 positioned on end cap 333. In other embodiments, button 452 may be positioned at a different location of shielded container 402, or the locking mechanism may be released in a different manner.

Returning to FIG. 4A, shielded container 402 may have a length 430, which may be greater than or equal to a length 431 of collimated line source 331. In one embodiment, length 430 is equal to length 431, and shielded container 402 may enclose collimated line source 331 such that when collimated line source 331 is positioned within shielded container 402, an outer surface of end cap 334 of collimated line source 331 may be flush with an outer surface of a second end 420 of shielded line source 331. In other embodiments, length 431 of collimated line source 331 may be less than length 430, such that when collimated line source 331 is positioned within shielded container 402, the outer surfaces of either or both of end cap 333 and end cap 334 may not be flush with an outer surfaces of first end 419 and second end 420, respectively.

Shielded container 402 may have an outer diameter 410. A cylindrical wall 432 of shielded container 402 may have a thickness 416, where thickness 416 is a difference between outer diameter 410 and inner diameter 412 of shielded container 402. Thickness 416 may be selected to ensure that radiation photons emitted by line source 332 of collimated line source 331 are absorbed by cylindrical wall 432 and do not pass through cylindrical wall 432 into an environment of shielded container 402.

For storage of collimated line source 331, collimated line source 331 may be slidably inserted into the internal space 406 of shielded container 402. Collimated line source 331 may be positioned such that central axis 348 of collimated line source 331 is aligned with a central axis 408 of shielded container 402, and collimated line source 331 may be slid in a first direction 436 into shielded container 402. When collimated line source 331 is slid into shielded container 402, outer wall 422 of end cap 333 and outer wall 423 of end cap 334 may be in face-sharing contact with inner wall 421 of collimated line source 331. When collimated line source 331 is used for calibrating the SPECT system, collimated line source 331 may be slid in a second direction 438 to be removed from shielded container 402.

In some embodiments, collimated line source 331 may be completely removed from shielded container 402. In other embodiments, collimated line source 331 may not be completely removed from shielded container 402, and collimated line source 331 may be partially removable from the shielded container, where a portion of collimated line source 331 may remain coupled to or connected to a corresponding portion of shielded container 402. For example, when collimated line source 331 is partially removed or withdrawn from shielded container 402, a portion of end cap 334 of the collimated line source may remain within shielded container 402, such that collimated line source 331 may be prevented from being completely removed from shielded container 402. When collimated line source 331 is partially removed from shielded container 402 with the portion of end cap 334 remaining within shielded container 402, an entirety of collimator plates 335 may be exposed, and no collimator plates 335 may remain within shielded container 402. An advantage of not allowing collimated line source 331 to be completely removed from shielded container 402 is that shielded container 402 may be maintained within a close proximity to collimated line source 331, and in a configuration that facilitates an easy and efficient insertion of collimated line source 331 into shielded container 402.

When collimated line source 331 is contained within shielded container 402, the radiation photons emitted by line source 332 may be absorbed by cylindrical wall 432, end cap 333, and end cap 334, and no radiation photons may be released into the environment of collimated line source 331. When collimated line source 331 is removed from shielded container 402, the radiation photons emitted by line source 332 may be absorbed by end cap 333 and end cap 334, but may not be absorbed by cylindrical wall 432, whereby radiation photons may be released into the environment of collimated line source 331. However, because of the collimator plates 335, the radiation photons may be released into the environment in the perpendicular direction, and not in other directions. As a result, an amount of radiation released into the environment by collimated line source 331 may be greatly reduced with respect to a line source not including collimator plates 335 (e.g., line source 303 of FIG. 3A).

In some embodiments, during calibration of the SPECT system, a technician or operator of the SPECT system may retrieve collimated line source 331 from a storage location, where collimated line source 331 is stored within shielded container 402. The technician may place shielded container 402 including collimated line source 331 on a table of the SPECT system (e.g., table 120). The technician may manually remove collimated line source 331 from shielded container 402, by sliding collimated line source 331 out of shielded container 402 in second direction 438. After sliding collimated line source 331 out of shielded container 402, the technician may be temporarily exposed to radiation emitted from collimated line source 331. The technician may adjust a position of the table via a controller (e.g., table controller 134) and/or a gantry of the SPECT system (e.g., gantry 104) via a gantry controller (e.g., gantry motor controller 132), such that collimated line source 331 is positioned within and/or surrounded by a plurality of detector arrays of the SPECT system. The SPECT system may then collect calibration data via the detector arrays, and the technician may leave an unshielded area of the SPECT system to reduce the exposure to radiation. After a sufficient amount of calibration data has been collected, or at an end of an availability of the SPECT system for collecting the calibration data, the technician may adjust the position of the table and/or gantry to remove collimated line source 331 from the SPECT system. The technician may slide collimated line source 331 into shielded container 402 in the first direction 436 to insert collimated line source 331 into shielded container 402. After collimated line source 331 is inserted into shielded container 402, the technician may not be exposed to radiation emitted from collimated line source 331. The technician may store collimated line source 331 within shielded container 402 at the storage location.

In preferred embodiments, during calibration of the SPECT system, collimated line source 331 may not be retrieved manually from the storage location and placed on the table, and collimated line source 331 may be retrieved from the storage location and positioned within the SPECT system without manual intervention. For example, the storage location may be a compartment within a bed of the SPECT system, and one or more components of the SPECT system may extract collimated line source 331 from the compartment and position collimated line source 331 within a gantry of the SPECT system for collecting the calibration data. The SPECT system may also remove collimated line source 331 from shielded container 402.

In one embodiment, collimated line source 331 is retractable and stored in a compartment within the table. Collimated line source 331 may be slid out of the compartment and extended into the gantry for collecting the calibration data. In such embodiments, the technician may not be temporarily exposed to radiation emitted from collimated line source 331. After a sufficient amount of calibration data has been collected, or at an end of the availability of the SPECT system for collecting the calibration data, collimated line source 331 may be inserted into shielded container 402 and/or may be stored in the compartment by the SPECT system, without manual intervention. For example, collimated line source 331 may be retracted into the compartment of the bed by the SPECT system.

FIGS. 7A and 7B depict an example of a retractable collimated line source stored in a bed of a table of a SPECT system, as described above. Turning to FIG. 7A, a multi-head SPECT system 700 is shown during a scan of a patient 708, which may be a non-limiting example of NM imaging systems 100 and/or 200 of FIGS. 1A and 2A, respectively. SPECT system 700 includes a bed or table base 706 positioned proximate a gantry 704. Various detector heads may be positioned within gantry 704, of which an upper detector head 710 is depicted with a detector unit 712 (e.g., detector units 114 of FIGS. 1A and 1B), and a lower detector head 716 is depicted with a detector unit 714. Upper detector head 710 and lower detector head 716 are aligned along vertical axis 292.

A moveable table 707 (e.g., table 120) of table base 706 has been extended into a bore 702 (e.g., aperture 118) of gantry 704, in a direction 755, along horizontal axis 291. As a result, patient 708 on moveable table 707 is positioned within an imaging plane of gantry 704, such that photons emitted by a radioactive tracer introduced into a head of patient 708 may be detected at a plurality of rotating detector units of SPECT system 700, including detector units 712 and 714. Table base 706 is adjusted to a first height 732 with respect to a floor 709, via an adjustable support system 730. Adjustable support system 730 may comprise any type or configuration of legs, supports, and/or motors of table base 706 that may allow table base 706 to be selectively adjusted to a variety of heights. For example, first height 732 may be selected based on SPECT system 700 being used for a scan of patient 708, and/or a size of patient 708. Specifically, first height 732 may be selected to position patient 708 along a central axis 715 (e.g., along horizontal axis 291) of bore 702.

Table base 706 includes a compartment 718, which houses a collimated line source 720, which may be a non-limiting example of collimated line source 331 of FIGS. 3B-4A. Compartment 718 may include a retraction apparatus 721, which may extract collimated line source 720 from compartment 718 and/or retract collimated line source 720 into compartment 718 during calibration of SPECT system 700. In the depicted embodiment, retraction apparatus 721 includes a guide rod 719 and a motor 722, where collimated line source 720 is slidably coupled to motor 722 via guide rod 719. Motor 722 may be activated in a first direction to slide collimated line source 720 out of compartment 718, and motor 722 may be activated in a second direction to slide collimated line source 720 into a retracted position within compartment 718. However, it should be appreciated that in other embodiments, a different retractable apparatus 721 may be used to extract and retract collimated line source 720 from compartment 718. For example, in other embodiments, a sliding panel in a surface of table 707 may open, and a surface of compartment 718 on which collimated line source 720 rests may be raised to a level of the surface of the table for collecting calibration data.

FIG. 7B shows a second configuration 750 of SPECT system 700, where a scan of a patient is not being performed, and collimated line source 720 is being used to calibrate SPECT system 700. In second configuration 750, adjustable support system 730 has been adjusted in a direction 757 (e.g., along vertical axis 292) such that table base 706 is at a second height 752 with respect to floor 709. Second height 752 may be greater than first height 732. At second height 752, table base 706 may be positioned such that compartment 718 is vertically aligned with central axis 715 of bore 702.

In FIG. 7B, collimated line source 720 has been extracted from an external shielding 754 of collimated line source 720 (e.g., shielded container 402 of FIGS. 4A and 4B) and positioned within gantry 704. For example, collimated line source 720 may be positioned along central axis 715, or at a position close to central axis 715 aligned with horizontal axis 291. At the depicted position, detector units including detector units 712 and 714 may detect photons emitted by collimated line source 720, as described above in reference to FIG. 3B. Specifically, collimated line source 720 may be coupled to an end of guide rod 719, and motor 722 may actuate guide rod 719 in direction 755 such that collimated line source 720 is slid at least partially out of external shielding 754 and positioned within gantry 704. For example, motor 722 may actuate guide rod 719 to position collimated line source 720 within gantry 704 based on a command inputted into SPECT system 700 by an operator of SPECT system 700 via an input device of SPECT system 700 (e.g., input device 166 of FIG. 1A). In some embodiments, actuate guide rod 719 in direction 755 may include opening a panel or door 756 of compartment 718.

After a calibration procedure using collimated line source 720 has concluded, motor 722 may actuate guide rod 719 in a direction 751, such that collimated line source 720 is slid into external shielding 754 and positioned within compartment 718. Motor 722 may actuate guide rod 719 to position collimated line source 720 within compartment 718 based on a command inputted into SPECT system 700 by the operator, or motor 722 may actuate guide rod 719 to position collimated line source 720 within compartment 718 after a completion of the calibration procedure.

While a multi-head SPECT system is depicted in FIGS. 7A and 7B, it should be appreciated that a similar procedure may be used to perform a calibration of a dual-head SPECT system (e.g., dual-head configuration 250). With a dual-head SPECT system, the gantry may be rotated such that detector heads of the SPECT system may be aligned vertically along axis 292 on each side of table base 706, and adjustable support system 730 may be actuated in direction 757 or a direction 753 to sweep collimated line source 720 vertically across the detector heads.

In other embodiments, compartment 718 may not be located in table base 706. For example, compartment 718 may be located in floor 709, and retraction apparatus 721 may extend collimated line source 720 up in direction 757 along vertical axis 292 to height 752, and retract collimated line source 720 in direction 753 back into compartment 718 after calibration has concluded. In such embodiments, table base 706 may be moved away from gantry 704 prior to using collimated line source 720.

FIG. 4C shows an alternative configuration 470 of collimated line source 331, where additional shielding is included in one or more side portions of collimated line source 331. In alternative configuration 470, line source 332 and collimated plates 335 are covered and partially enclosed by a first shielding portion 472 and a second shielding portion 474. For example, first shielding portion 472 may cover a top section of collimated line source 331, and second shielding portion 474 may cover a bottom section of collimated line source 331. In this way, one or more windows 476 may be created along a middle section of collimated line source 331, where window 476 is aligned with central axis 348. For example, in the depicted configuration, a first window 476 may be created on a first, visible side of collimated line source 331, and a second window 476 may be created on a second, obscured side of collimated line source 331. In other embodiments, a greater or lesser number of windows 476 may be created by a greater or lesser number of shielding portions. For example, three, or four, or more windows 476 may be created by shielding portions distributed around an outer circumference of collimated line source 331.

Specifically, each of first shielding portion 472 and second shielding portion 474 may have an outer circumferential surface that is flush with outer wall 422 of end cap 333 and outer wall 423 of end cap 334. In other words, an outer diameter of a cylinder partially formed by first shielding portion 472 and second shielding portion 474 may be equal to outer diameter 414 of end caps 333 and 334. Thus, as the depicted embodiment of collimated line source 331 is inserted into shielded container 402, the outer circumferential surface may be in face sharing contact with inner wall 421 of shielded container 402.

First shielding portion 472 and second shielding portion 474 may be manufactured out of a similar material as collimator plates 335 and/or shielded container 402, such that photons emitted by line source 332 may be absorbed by first shielding portion 472 and second shielding portion 474.

Window 476 has a height 480 and a length 482, where in different embodiments either or both of height 480 and length 482 may be greater or less than depicted in FIG. 4C. Thus, radiation photons emitted by line source 332 may pass through window 476 (e.g., to be detected by detector arrays of the SPECT system). However, the radiation photons emitted by line source 332 may not pass through first shielding portion 472 and second shielding portion 474. An advantage of including first shielding portion 472 and second shielding portion 474 on collimated line source 331 is that less radiation may be emitted into the environment during calibration when collimated line source 331 is removed from shielded container 402, while permitting photons to be directed towards one or more detector heads. The radiation photons emitted through window 476 may be sufficient for calibrating the SPECT system, as described below in reference to FIG. 5.

FIG. 5 shows a radiation emission diagram 500 showing a front view perspective of a dual-head SPECT system 501 (e.g., NM imaging system 100 of FIG. 1A and dual head configuration 250 of FIG. 2B) during calibration using a collimated line source 502, which may be a non-limiting example of collimated line source 331 of FIGS. 3A-4B. First radiation emission diagram 500 shows a first head 520 and a second head 522 positioned vertically on a gantry of the SPECT system, such that first head 520 and second head 522 may rotate around collimated line source 502 in an imaging plane. First head 520 and second head 522 may be non-limiting examples of first head 252 and second head 254 of FIG. 2B.

First head 520 includes a first detector array 510 having a plurality of detector elements 508 (e.g., pixels), and second head 522 includes a second detector array 524 having a plurality of detector elements 526. Collimated line source 502 may be positioned within dual-head SPECT system 501, such that collimated line source 502 is aligned coaxially with a central axis of first head 520 and a second head 522. For example, collimated line source 502 may be placed on a table 505, or extended out from a base of table 505, as described in greater detail below in reference to FIGS. 7A and 7B. Thus, collimated line source 502 may be adjusted upward in a direction indicated by an arrow 570 or downward in a direction indicated by an arrow 571 by adjusting a position of table 505 up or down. Collimated line source 502 includes a line source 504 (e.g., line source 332) that emits a plurality of radiation photons 506 that may be detected by detector elements 508 and/or detector elements 526 as first head 520 and a second head 522 are rotated around collimated line source 502.

In the depicted embodiment, collimated line source 502 includes additional portions of shielding, such as the embodiment depicted in FIG. 4C. Specifically, collimated line source 502 may include a first shielding portion 552 (e.g., first shielding portion 472) and a second shielding portion 554 (e.g., second shielding portion 474) on an outer circumference of collimated line source 502. First shielding portion 552 and second shielding portion 554 may create a first window 560 at a first side of collimated line source 502, and a second window 562 at a second side of collimated line source 502. Thus, radiation photons emitted by a line source 504 of collimated line source 502 may pass through either or both of first window 560 and second window 562. However, radiation photons emitted by line source 504 may not pass through first shielding portion 552 and second shielding portion 554. Thus, a smaller number of photons may be emitted by collimated line source 502 including first shielding portion 552 and second shielding portion 554 than by other configurations of collimated line source 331 not including first shielding portion 552 and second shielding portion 554. In particular, first window 560 and second window 562 may be positioned such that photons emitted by line source 504 that would not otherwise impinge on first detector array 510 or second detector array 524 (e.g., photons that would be emitted into a room of dual-head SPECT system 501 and would not be used for calibration) are absorbed by either first shielding portion 552 and second shielding portion 554. Because heads 520 and 522 may rotate around collimated line source 502, the photons passing through first window 560 and/or second window 562 may be detected at various detector elements 508 and/or 560. Thus, as a result of the first shielding portion 552 and second shielding portion 554, the decreased number of photons emitted by collimated line source 502 may reduce an amount of radiation released during calibration.

Referring now to FIG. 6, a method 600 is shown for calibrating a SPECT system, such as SPECT system 100 of FIG. 1A or other embodiments of a SPECT system described herein. Method 600 may be performed by a control unit of the SPECT system, such as control unit 130 of FIG. 1A. Additionally, some steps of method 600 may be performed by an operator or technician of the SPECT system, using a collimated line source such as collimated line source 331 of FIGS. 3B-4C.

Method 600 begins at 602, where method 600 includes determining whether the SPECT system is available for collecting calibration data. The calibration data may be collected over a plurality of data collection sessions when the SPECT system is available for collecting calibration data. For example, the SPECT system may be available for collecting calibration data during a data collection session when the SPECT system is not in use during an examination of a subject, or when maintenance is being performed on one or more components of the SPECT system. The data collection sessions may be short increments of time between examinations. For example, a first examination of a first subject may have ended, and a second examination of a second subject may not yet have begun, where there may be an amount of time available for collecting calibration data between an end of the first examination and a beginning of the second examination. For example, the data collection session (e.g., the increment of time) may be five minutes, or ten minutes, or a different amount of time. The SPECT system may also be available for collecting calibration data, for example, if a scheduled examination is canceled or postponed, or during periods of time before and/or after a typical daily use of the SPECT system.

If at 602 it is determined that the SPECT system is not available for collecting calibration data, method 600 proceeds to 603. At 603, method 600 includes waiting until the SPECT system is available.

If at 602 it is determined that the SPECT system is available for collecting calibration data, method 600 proceeds to 604. At 604, method 600 may include indicating an availability of the SPECT system for calibration to an operator of the SPECT system, or other technician of the SPECT system. For example, the availability may be indicated via a display element on a display device of the SPECT system, and/or an indicator light on a different component of the SPECT system.

When the availability of the SPECT system is indicated, the operator or other technician may initiate a procedure for collecting calibration data. In some embodiments, the operator or other technician may manually retrieve the collimated line source from a storage location of the collimated line source. The operator or other technician may manually place the collimated line source on a bed or table (e.g., table 120) of the SPECT system. In various (e.g., preferred) embodiments, the collimated line source may be stored in a compartment of the SPECT system. For example, the collimated line source may be stored in a compartment of the SPECT system located in a base of the bed or table, as described above in reference to FIGS. 7A and 7B. The collimated line source may be stored in a shielded container, such as shielded container 402 of FIGS. 4A-4C, to ensure that radiation emitted by the collimated line source is not released into a room of the SPECT system when the calibration data is not being collected.

In various embodiments, the collimated line source may be extracted from the compartment located in the base of the bed by the SPECT system. For example, in response to the availability of the SPECT system being indicated, the operator or other technician may select a control element on the display device for extracting the collimated line source. In response to the operator or other technician selecting the control element, the collimated line source may be extracted from the compartment and placed on within a gantry of the SPECT system (e.g., the retraction apparatus 721 of FIGS. 7A and 7B). For example, the collimated line source may be stored in a compartment of the table, such that the collimated line source may be retracted into the table when not used for collecting calibration data. After the calibration data has been collected, the collimated line source may be retracted into the compartment and/or into a shielded container of the collimated line source. In other embodiments, the collimated line source may be placed on the table using one or more robotic arms of the SPECT system, or in a different manner.

At 606, method 600 includes removing the collimated line source from the shielded container. In some embodiments, the operator or technician may manually remove the collimated line source from the shielded container. For example, the operator or technician may release a locking mechanism of the collimated line source by pressing a button (e.g., button 452 of FIG. 4B), allowing the collimated line source to be slid out of the shielded container. In some embodiments, the collimated line source may be completely removed from the shielded container. In other embodiments, the collimated line source may be partially removed from the shielded container such that a portion of the collimated line source may remain coupled to or connected to a corresponding portion of the shielded container. For example, a portion of an end cap (e.g. end cap 334) of the collimated line source may remain within the shielded container, such that the collimated line source may be prevented from being completely removed from the shielded container.

In preferred embodiments, the collimated line source may be removed or partially withdrawn from the shielded container by the SPECT system without manual intervention. For example, a robotic arm of the SPECT system may slide the collimated line source out of the shielded container, or a retractable apparatus of the table may be configured to slide the collimated line source out of the shielded container. In other embodiments, the collimated line source may be removed or partially withdrawn from the shielded container in a different manner.

When the collimated line source is removed or partially withdrawn from the shielded container, radiation emitted by the collimated line source may be released into the SPECT system and/or a room of the SPECT system. However, a first amount of radiation emitted by the collimated line source may be substantially less than a second amount of radiation emitted by an alternative non-collimated source of radiation.

At 608, method 600 includes positioning the shielded collimated line source within detector units (e.g., detector units 114 of FIG. 1A) of the SPECT system. Positioning the shielded collimated line source within the detector arrays may include adjusting a position of the table of the SPECT system via a table controller of the SPECT system (e.g., table controller 134 of FIG. 1A). Positioning the shielded collimated line source within the detector arrays may include adjusting a position of a gantry (e.g., gantry 104) of the SPECT system via a gantry controller of the SPECT system (e.g., gantry motor controller 132). Positioning the shielded collimated line source within the detector arrays may also include adjusting a height of the table, for example, via an adjustable support system of the table (e.g., adjustable support system 730 of FIGS. 7A and 7B).

At 610, method 600 includes acquiring calibration data using the collimated line source. The calibration data may be collected based on electrical signals generated at a plurality of detector elements of the detector arrays of the SPECT system, as described above. As the electrical signals are generated at the plurality of detector elements, the electrical signals may be converted to digital readings by the SPECT system, and the digital readings may be stored by the SPECT system for a later calibration of the SPECT system. For example, the digital readings may be stored in data storage device 164 of NM imaging system 100 of FIG. 1A. In various embodiments, the calibration data collected using the collimated line source may be aggregated with or added to calibration data previously collected during previous data collection sessions.

At 612, method 600 includes determining whether the SPECT system is no longer available for collecting calibration data. For example, the SPECT system may no longer be available for collecting calibration data due to being scheduled for a next patient examination, or a different use. If at 612 it is determined that the SPECT system is still available for collecting calibration data, method 600 proceeds back to 610, and the SPECT system continues acquiring the calibration data using the collimated line source. Alternatively, if at 612 it is determined that the SPECT system is no longer available for collecting calibration data, method 600 proceeds to 614. At 614, at the 600 includes stopping acquiring and collecting the calibration data.

In some embodiments, the collected calibration data may be used to retroactively correct images generated by the SPECT system prior to calibrating the SPECT system. The reconstruction algorithm uses raw data measured by the SPECT system, together with calibration data of the SPECT system to obtain a desired image. The image can be produced instantly at a first time, so a technician can verify that the scan was successful, and then saved for physician to examine and make medical observations at a second time, which may be much later, often not the same day of scan. However, raw data from the scan can be saved and image can be reproduced later for physician to examine. If a calibration is performed between the first time and the second time, more recent calibration data can be used in the image reconstruction, which may generate an image of increased quality.

At 616, method 600 includes removing the shielded line source from the SPECT system and storing it until next opportunity for collecting additional calibration data. In some embodiments, the shielded line source may be manually removed from the SPECT system by the operator or technician and placed in the storage compartment until the next opportunity. In other embodiments, the shielded line source may be removed from the SPECT system and placed in the storage compartment by the SPECT system. For example, the shielded line source may be retracted into a compartment in a portion of the table, as described above. When the shielded line source is stored in the compartment, no radiation may be emitted into the room. In some embodiments, the compartment may include shielding, whereby the collimated line source may not be stored in the shielded container prior to being stored in the compartment.

Because the amount of available time for collecting the calibration data may be small (e.g., five or 10 minutes) an amount of calibration data collected by the SPECT system may not be sufficient for calibrating operating parameters of the SPECT system. As a result, additional calibration data may be collected at other opportunities during which the SPECT system is not in use. For example, a first amount of calibration data may be collected during a first calibration data collection session; where the first amount of calibration data may not be sufficient for calibrating the SPECT system; a second amount of calibration data may be collected during a second calibration data collection session and aggregated with the first amount of calibration data, where the aggregated amount of calibration data may not be sufficient for calibrating the SPECT system; a third amount of calibration data may be collected during a third calibration data collection session and aggregated with the first and second amounts of calibration data, where the aggregated amount of calibration data may not be sufficient for calibrating the SPECT system; and so on, until the sufficient amount of calibration data has been collected. Each calibration data collection session may have a different duration. For example, a total amount of time used to collect the sufficient amount of calibration data may be three hours, where the sufficient amount of calibration data may be collected over 15-20 calibration data collection sessions, where each calibration data collection session occurs over a different amount of time between 5 and 10 minutes.

At 618, method 600 includes inserting the collimated line source back in the shielded container. In some embodiments, the collimated line source may be inserted into the shielded container manually by the operator or technician. In other embodiments, the collimated line source may be inserted into the shielded container by one or more components of the SPECT system, as described above. After the collimated line source is inserted into the shielded container, the radiation emitted by the collimated line source may be absorbed by the shielded container, and no radiation may be released into the room.

At 620, method 600 includes determining whether sufficient calibration data has been collected. If at 620 it is determined that a sufficient amount of calibration data has not been collected, method 600 proceeds back to 603, and method 600 includes waiting for a next opportunity to collect additional calibration data. If at 620 it is determined that the sufficient amount of calibration data has been collected, method 600 proceeds to 622.

At 622, method 600 includes calibrating the SPECT system using the collected calibration data. First, an energy calibration may be performed, in which a conversion from electronic readout to energy is determined. For each pixel in the detector array, the electronic readout provides an amplitude of a pulse produced by a detector element in response to an event (e.g., an impinging photon). The amplitude is linearly proportional to an energy of the photon detected, and the calibration establishes the coefficients of this linear relation. Thus, the energy calibration requires one or more calibration sources emitting at known energies, such as, for example, Co-57 emitting at 122 KeV surrounded by a tungsten sleeve producing emissions at 80 KeV. The calibration algorithm histograms the electronic readouts and detects peak energy positions. The linear coefficients can be determined for the electronic readout to energy conversion by matching the peak positions to the appropriate KeV.

During the scan, events measured within an energy window (e.g., typically ±10% of the known emission energy) may be considered, and events measured outside the energy window may not be considered. If an energy calibration is inaccurate, part of the events will be outside the energy window, since their calculated energy will be wrong. As a result, achieving a desired image quality may depend on correcting an inaccurate energy calibration.

A uniformity calibration may also be performed, to ensure that the pixels in the detector array have a uniform sensitivity. Natural variations in the pixels produce different sensitivity with respect to radiation detection. Because a reconstruction algorithm used may assume uniform response, non-uniformity may produce artifacts in the image. Thus, the uniformity calibration includes exposing the detectors and measuring counts detected within the energy window based on the energy calibration. This is done per pixel to produce a correction map (e.g., a mapping of the sensitivity). The correction map can then be applied to the counts. Shifts in energy calibration, as stated above, will change the number counts in the energy window, thus changing the uniformity calibration and causing artifacts in a resulting image. Method 600 ends.

Thus, a novel configuration of a collimated radioactive line source for calibrating a SPECT system is proposed, the radioactive line source including a plurality of collimator plates that may reduce an amount of radiation emitted by radioactive material of the collimated line source without affecting a collection of calibration data based on the collimated line source. The collimator plates are configured in parallel around the radioactive material, such that photons emitted by the radioactive material in angles perpendicular to the collimated line source pass through the collimator plates, and photons emitted by the radioactive material in angles other than perpendicular to the collimated line source are absorbed by the collimator plates. Because a majority of photons are emitted at angles other than perpendicular to the collimated line source, less radiation may be released into an environment of the SPECT system than a non-collimated line source. For example, while a typical line source not including collimator plates may release a large amount of radiation (e.g., 100 million photons per second) into the environment of the SPECT system, the collimated line source described herein may release significantly less radiation into the environment of the SPECT system (e.g., less than a radiation level defined by a regulator as safe for the general public). Because the photons emitted at angles other than perpendicular would not be detected at a collimated detector array of the SPECT system, an effect on collection of calibration data may be negligible. By reducing the amount of radiation released into the environment, a safety of operators, technicians, caregivers, and/or subjects of the SPECT system may be increased.

The amount of radiation released into the environment may be further reduced by storing the collimated line source in a shielded container, where the collimated line source may be quickly and efficiently removed for collecting calibration data, and re-inserted into the shielded container for storage before and after the collection of calibration data. In some embodiments, the collimated line source may be stored in a compartment of the SPECT system, and the collimated line source may be positioned on a table of the SPECT system and/or removed from the shielded container by the SPECT system without manual intervention. For example, the compartment may be located in a retractable portion of the table.

The reduced amount of radiation may decrease an amount of time that the SPECT system is unavailable due to radiation exposure concerns. In other words, the reduction in radiation emitted by the proposed collimated line source (with respect to a non-collimated line source) may increase an amount of time that the operators, technicians, caregivers, and/or subjects of the SPECT system can be in the environment of the SPECT system while the collimated line source is being used to collected calibration data. Because of the reduced radiation, increments of time between patient examinations may be advantageously used to collect the calibration data, where previously the increments of time may not have been sufficient to perform the tasks inherent to collecting the calibration data while simultaneously minimizing exposure of humans in the environment to radiation. As a result, rather than scheduling a prolonged period of time (e.g., several hours) for performing periodic calibrations, data for performing the periodic calibrations may be collected piecemeal during the time increments. When a sufficient amount of data has been collected to perform the calibration, the SPECT system may be calibrated in a shorter procedure than currently used by the periodic calibrations. In this way, waiting time between patient scans that was previously unused can be used productively to increase an overall availability of the SPECT system for the patient exams.

The technical effect of including collimator plates on a line source is that an amount of radiation released into an environment of a SPECT system during calibration may be reduced, allowing small increments of time to be advantageously used to collect calibration data for the SPECT system.

The disclosure also provides support for a collimated line source for calibrating a single photon emission computed tomography (SPECT) imaging system, the collimated line source comprising a radioactive material aligned along a central axis of the collimated line source and a plurality of collimator plates arranged perpendicularly around the central axis, the collimator plates including a material with an atomic number and a density to substantially absorb photons striking the collimator plates. In a first example of the system, the collimator plates are made of one of lead, tungsten, or molybdenum. In a second example of the system, optionally including the first example, the collimator plates are evenly spaced along the central axis. In a third example of the system, optionally including one or both of the first and second examples, the collimator plates have a circular, disc shape, and the collimated line source has a cylindrical shape. In a fourth example of the system, optionally including one or more or each of the first through third examples, the collimated line source includes a first end cap at a first end of the collimated line source, and a second end cap at a second, opposing end of the collimated line source, the first end cap and the second end cap including a same material as the collimator plates. In a fifth example of the system, optionally including one or more or each of the first through fourth examples, the collimated line source is coupled to a shielded container, and the collimated line source is partially removable from the shielded container to expose the collimator plates. In a sixth example of the system, optionally including one or more or each of the first through fifth examples, the system further comprises: one or more shielding portions that partially shield the plurality of collimator plates arranged perpendicularly around the radioactive material, the one or more shielding portions forming one or more windows through which photons emitted by the radioactive material pass.

The disclosure also provides support for a method for calibrating a single photon emission computed tomography (SPECT) imaging system, the method comprising: collecting calibration data of the SPECT imaging system using a collimated line source of radiation, during increments of time between performing patient examinations using the SPECT imaging system, while one or more persons are present in an environment of the SPECT imaging system, and after a sufficient amount of calibration data has been collected, calibrating the SPECT imaging system using the amount of collected calibration data. In a first example of the method, the collimated line source comprises a radioactive material aligned along a central axis of the collimated line source and a plurality of collimator plates arranged perpendicularly around the central axis, the collimator plates including a material that substantially absorbs photons emitted by the radioactive material. In a second example of the method, optionally including the first example, the collimator plates are circular discs, and the collimated line source has a cylindrical shape including shielding at a first end and a second end of the collimated line source. In a third example of the method, optionally including one or both of the first and second examples, the method further comprises: storing the collimated line source in a shielded container having a hollow cylindrical shape, an inner diameter of the shielded container equal to an outer diameter of the collimated line source. In a fourth example of the method, optionally including one or more or each of the first through third examples, the method further comprises: storing the collimated line source in a compartment in a base of a bed of the SPECT imaging system. In a fifth example of the method, optionally including one or more or each of the first through fourth examples, collecting calibration data using the collimated line source further comprises: in response to an operator of the SPECT imaging system selecting a control element on a display device of the SPECT imaging system: extracting the collimated line source from the compartment and positioning the collimated line source within a gantry of the SPECT imaging system for collecting the calibration data, and after the calibration data has been collected, retracting the collimated line source into the compartment. In a sixth example of the method, optionally including one or more or each of the first through fifth examples, extracting the collimated line source from the compartment and positioning the collimated line source within the gantry of the SPECT imaging system further comprises: adjusting a height of the bed such that the compartment is vertically aligned with a central axis of a bore of the gantry, removing the collimated line source from a shielded container, mechanically extending the collimated line source horizontally out of the compartment using a retraction apparatus included in the compartment. In a seventh example of the method, optionally including one or more or each of the first through sixth examples, the collected calibration data is used to retroactively correct images generated by the SPECT imaging system prior to calibrating the SPECT imaging system.

The disclosure also provides support for a single photon emission computed tomography (SPECT) imaging system, comprising: a collimated line source stored in a compartment of the SPECT imaging system, the collimated line source including a radioactive material aligned along a central axis of the collimated line source and a plurality of collimator plates arranged perpendicularly around the central axis that absorb photons emitted by the radioactive material, a controller including instructions stored in a memory of the SPECT imaging system, that when executed, cause the controller to: in response to a user input from an operator of the SPECT imaging system, extract the collimated line source from a compartment of the SPECT imaging system and position the collimated line source within a gantry of the SPECT imaging system, collect calibration data of the SPECT imaging system using the collimated line source, retract the collimated line source into the compartment after collecting the calibration data, and calibrate the SPECT imaging system based on the collected calibration data. In a first example of the system, the calibration data is collected during a calibration data collection session between an end of a first patient examination using the SPECT imaging system, and a beginning of a second patient examination using the SPECT imaging system. In a second example of the system, optionally including the first example, further instructions are stored in the memory that when executed, cause the controller to aggregate calibration data collected over a plurality of calibration data collection sessions, and calibrate the SPECT imaging system based on the aggregated calibration data. In a third example of the system, optionally including one or both of the first and second examples, extracting the collimated line source from the compartment further comprises extracting the collimated line source from a shielded container in which the collimated line source is stored when the collimated line source is not being used to collect the calibration data, and retracting the collimated line source into the compartment further comprises inserting the collimated line source into the shielded container. In a fourth example of the system, optionally including one or more or each of the first through third examples, an amount of radiation released by the collimated line source into a room of the SPECT imaging system during collection of the calibration data is less than a radiation level defined by a regulator as safe for the general public.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A collimated line source for calibrating a single photon emission computed tomography (SPECT) imaging system, the collimated line source comprising a radioactive material aligned along a central axis of the collimated line source and a plurality of collimator plates arranged perpendicularly around the central axis, the collimator plates including a material with an atomic number and a density to substantially absorb photons striking the collimator plates;

wherein the collimator plates have a circular, disc shape, and the collimated line source has a cylindrical shape.

2. The collimated line source of claim 1, wherein the collimator plates are made of one of lead, tungsten, or molybdenum.

3. The collimated line source of claim 1, wherein the collimator plates are evenly spaced along the central axis.

4. The collimated line source of claim 3, wherein the collimated line source includes a first end cap at a first end of the collimated line source, and a second end cap at a second, opposing end of the collimated line source, the first end cap and the second end cap including a same material as the collimator plates.

5. The collimated line source of claim 4, wherein the collimated line source is coupled to a shielded container, and the collimated line source is partially removable from the shielded container to expose the collimator plates.

6. The collimated line source of claim 1, further comprising one or more shielding portions that partially shield the plurality of collimator plates arranged perpendicularly around the radioactive material, the one or more shielding portions forming one or more windows through which photons emitted by the radioactive material pass.

7. A method for calibrating a single photon emission computed tomography (SPECT) imaging system, the method comprising:

collecting calibration data of the SPECT imaging system using a collimated line source of radiation, during increments of time between performing patient examinations using the SPECT imaging system, while one or more persons are present in an environment of the SPECT imaging system; and after a sufficient amount of calibration data has been collected, calibrating the SPECT imaging system using the amount of collected calibration data;

wherein the collimator plates are circular discs, and the collimated line source has a cylindrical shape including shielding at a first end and a second end of the collimated line source.

8. The method of claim 7, wherein the collimated line source comprises a radioactive material aligned along a central axis of the collimated line source and a plurality of collimator plates arranged perpendicularly around the central axis, the collimator plates including a material that substantially absorbs photons emitted by the radioactive material.

9. The method of claim 7, further comprising storing the collimated line source in a shielded container having a hollow cylindrical shape, an inner diameter of the shielded container equal to an outer diameter of the collimated line source.

10. The method of claim 7, further comprising storing the collimated line source in a compartment in a base of a bed of the SPECT imaging system.

11. The method of claim 10, wherein collecting calibration data using the collimated line source further comprises:

in response to an operator of the SPECT imaging system selecting a control element on a display device of the SPECT imaging system:

extracting the collimated line source from the compartment and positioning the collimated line source within a gantry of the SPECT imaging system for collecting the calibration data; and after the calibration data has been collected, retracting the collimated line source into the compartment.

12. The method of claim 11, wherein extracting the collimated line source from the compartment and positioning the collimated line source within the gantry of the SPECT imaging system further comprises:

adjusting a height of the bed such that the compartment is vertically aligned with a central axis of a bore of the gantry;

removing the collimated line source from a shielded container;

mechanically extending the collimated line source horizontally out of the compartment using a retraction apparatus included in the compartment.

13. The method of claim 7, wherein the collected calibration data is used to retroactively correct images generated by the SPECT imaging system prior to calibrating the SPECT imaging system.

14. A single photon emission computed tomography (SPECT) imaging system, comprising:

a collimated line source stored in a compartment of the SPECT imaging system, the collimated line source having a cylindrical shape including a radioactive material aligned along a central axis of the collimated line source and a plurality of circular, disc-shaped collimator plates arranged perpendicularly around the central axis that absorb photons emitted by the radioactive material;

a controller including instructions stored in a memory of the SPECT imaging system, that when executed, cause the controller to:

in response to a user input from an operator of the SPECT imaging system, extract the collimated line source from a compartment of the SPECT imaging system and position the collimated line source within a gantry of the SPECT imaging system;

collect calibration data of the SPECT imaging system using the collimated line source;

retract the collimated line source into the compartment after collecting the calibration data; and calibrate the SPECT imaging system based on the collected calibration data.

15. The SPECT imaging system of claim 14, wherein the calibration data is collected during a calibration data collection session between an end of a first patient examination using the SPECT imaging system, and a beginning of a second patient examination using the SPECT imaging system.

16. The SPECT imaging system of claim 15, wherein further instructions are stored in the memory that when executed, cause the controller to aggregate calibration data collected over a plurality of calibration data collection sessions, and calibrate the SPECT imaging system based on the aggregated calibration data.

17. The SPECT imaging system of claim 14, wherein extracting the collimated line source from the compartment further comprises extracting the collimated line source from a shielded container in which the collimated line source is stored when the collimated line source is not being used to collect the calibration data, and retracting the collimated line source into the compartment further comprises inserting the collimated line source into the shielded container.

18. The SPECT imaging system of claim 14, wherein the collimator plates are configured in parallel around the radioactive material, such that photons emitted by the radioactive material in angles perpendicular to the collimated line source pass through the collimator plates, and photons emitted by the radioactive material in angles other than perpendicular to the collimated line source are absorbed by the collimator plates.

* * * * *